United States Patent [19]

Nudell et al.

[11] Patent Number: 5,085,220
[45] Date of Patent: Feb. 4, 1992

[54] DOPPLER FLOW SENSING DEVICE AND METHOD FOR ITS USE

[75] Inventors: Bruce M. Nudell; Robert R. Entrekin, both of King County, Wash.; Robert Skidmore, Bitton; Nicholas P. Luckman, Bristol, both of Great Britain

[73] Assignee: SpaceLabs, Inc., Redmond, Wash.

[21] Appl. No.: 417,525

[22] Filed: Oct. 5, 1989

[51] Int. Cl.⁵ .............................................. A61B 8/06
[52] U.S. Cl. ........................... 128/661.09; 128/662.04
[58] Field of Search ............ 128/661.09, 661.1, 662.04

[56] References Cited

U.S. PATENT DOCUMENTS

| | | | |
|---|---|---|---|
| 3,977,247 | 8/1976 | Hassler | 128/661.1 X |
| 4,259,870 | 4/1981 | McLeod et al. | 128/661.1 X |
| 4,373,533 | 2/1983 | Iinuma | 128/661.1 X |
| 4,493,216 | 1/1985 | Hassler | 128/661.1 X |
| 4,519,260 | 5/1985 | Fu et al. | 128/661.1 X |
| 4,807,636 | 2/1989 | Skidmore et al. | 128/661.1 |
| 4,873,985 | 10/1989 | Nakajima | 128/661.09 |

Primary Examiner—Francis Jaworski
Attorney, Agent, or Firm—Seed and Berry

[57] ABSTRACT

A device for sensing blood flow in a human aorta and a method for its use. The device includes two arrays, each array including one or more ultrasonic transducers for transmitting and/or receiving ultrasonic pulses. By appropriate weighting and phasing of the two ultrasonic arrays, a wide beam for insonifying the entire aorta, and a narrow beam for insonifying only a portion of the interior of the aorta, are produced. In addition, signals from the arrays can be processed to produce a signal indicating the direction to move the device so that the wide beam insonifies the entire aorta and the narrow beam insonifies only an interior portion of the aorta. The direction-finding array can be made from sensors arranged in a north-south-east-west pattern or as four sectors of an annulus.

34 Claims, 18 Drawing Sheets

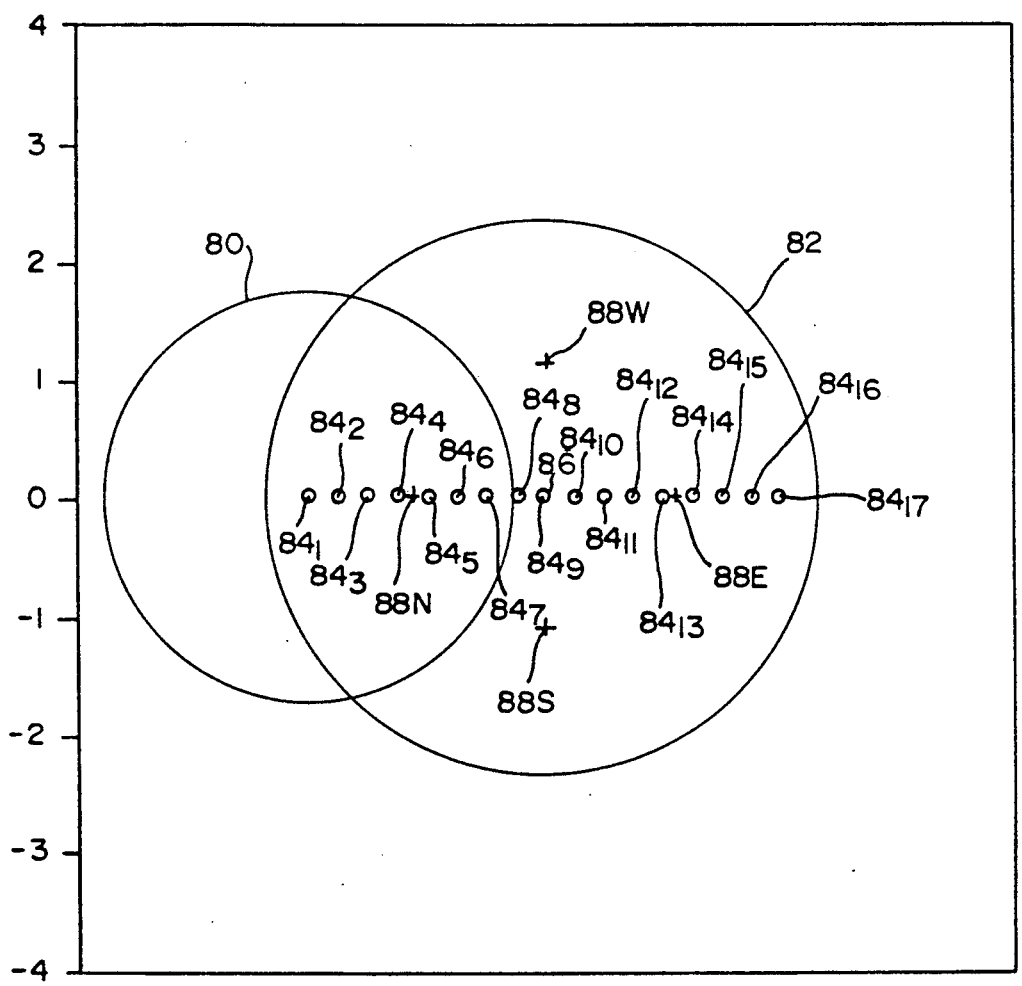

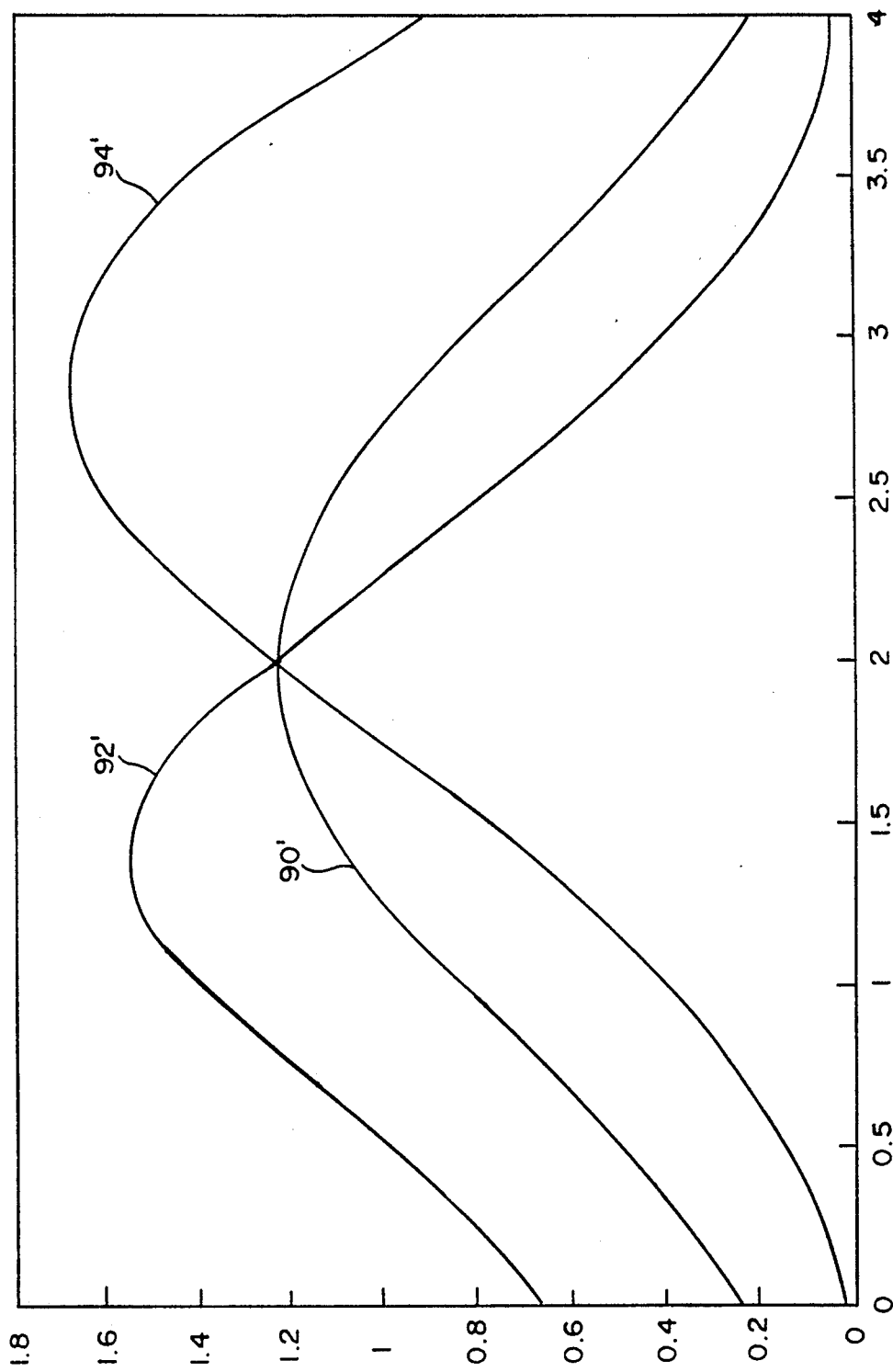

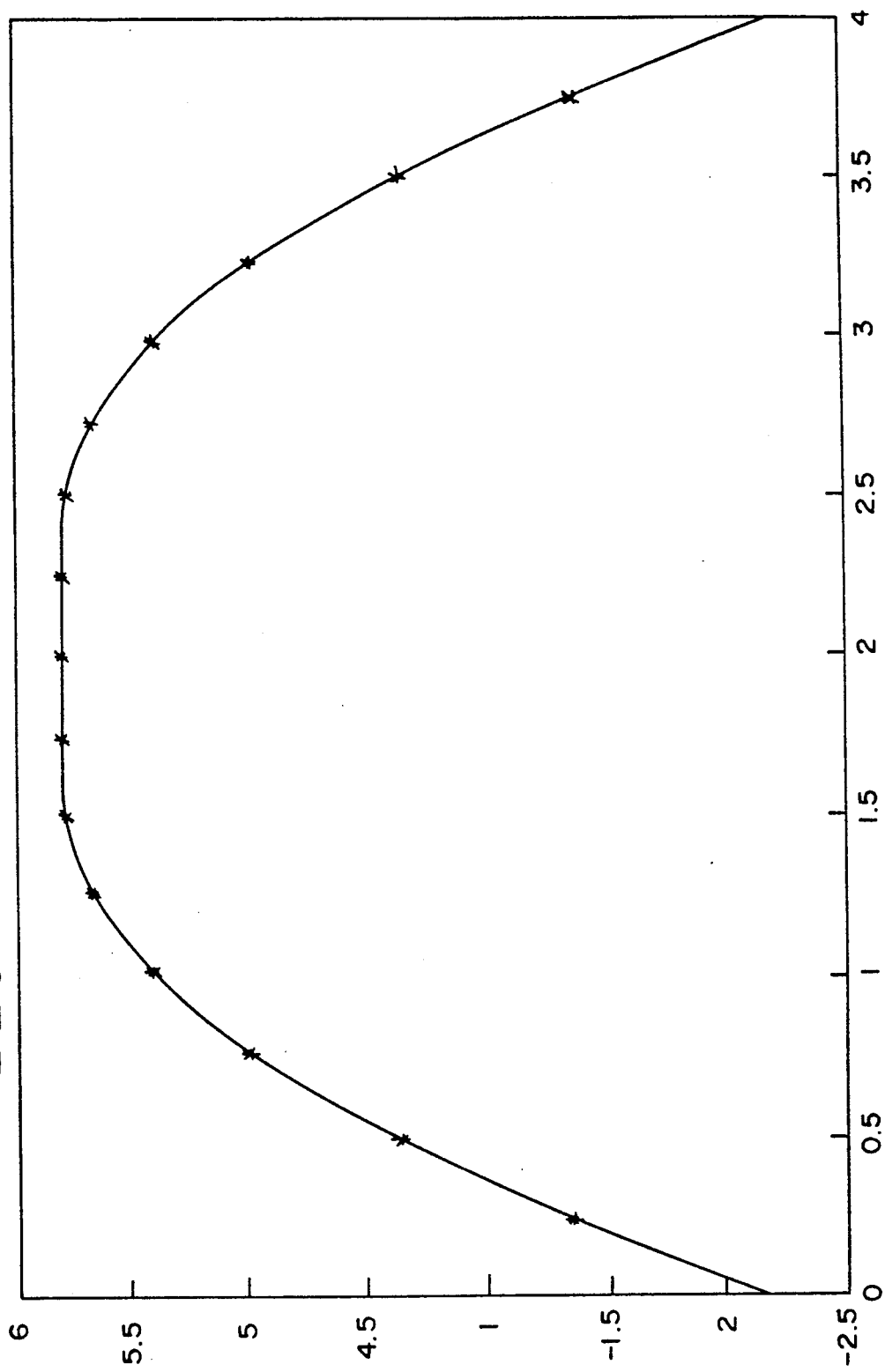

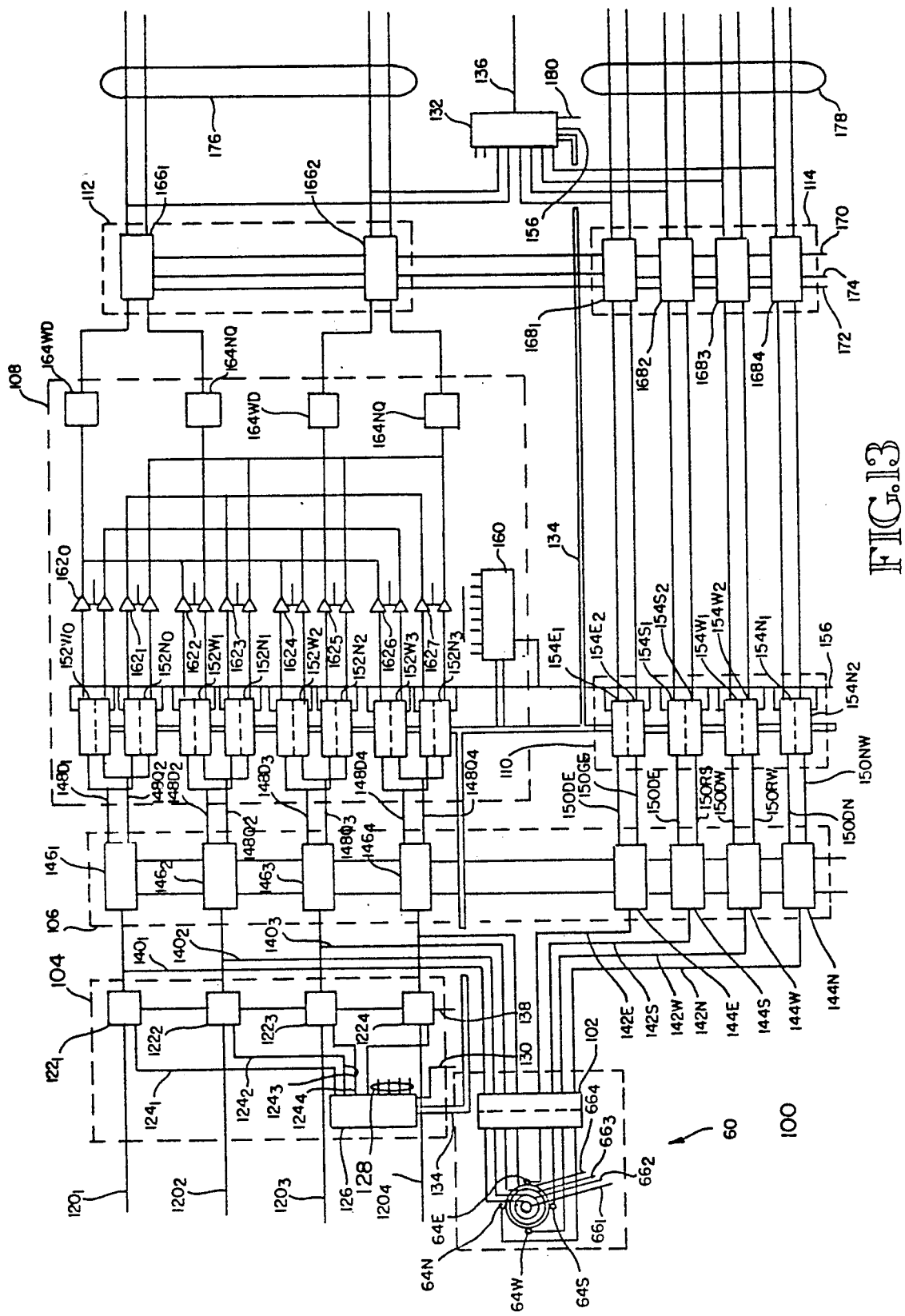

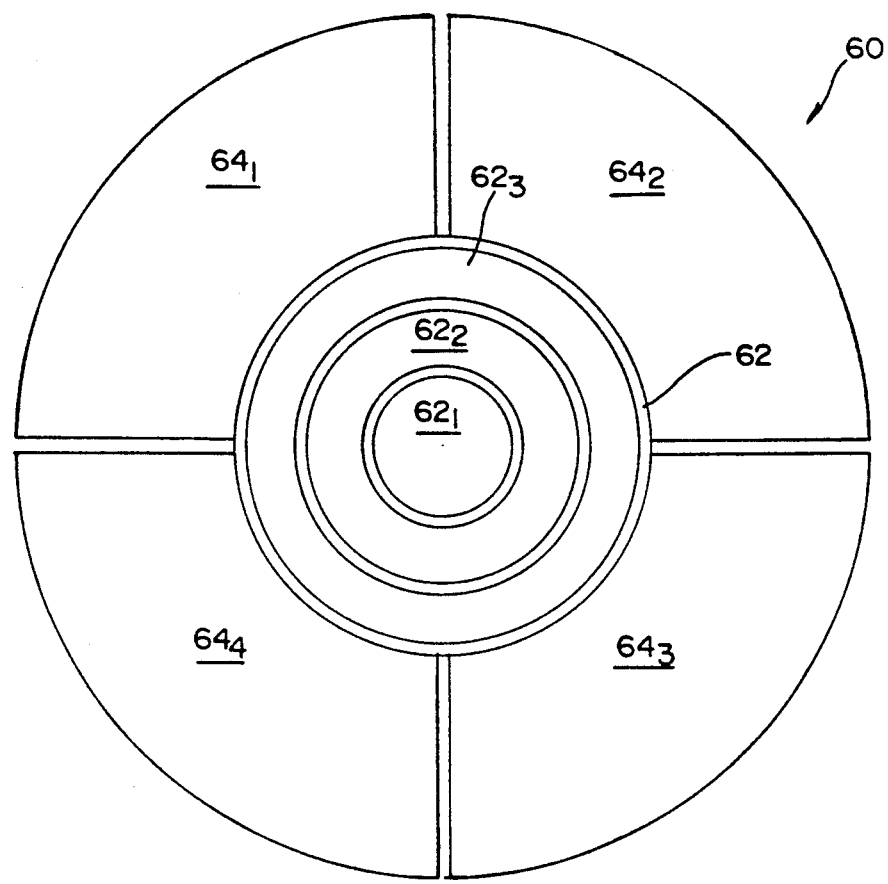
FIG. 14
FIG. 15
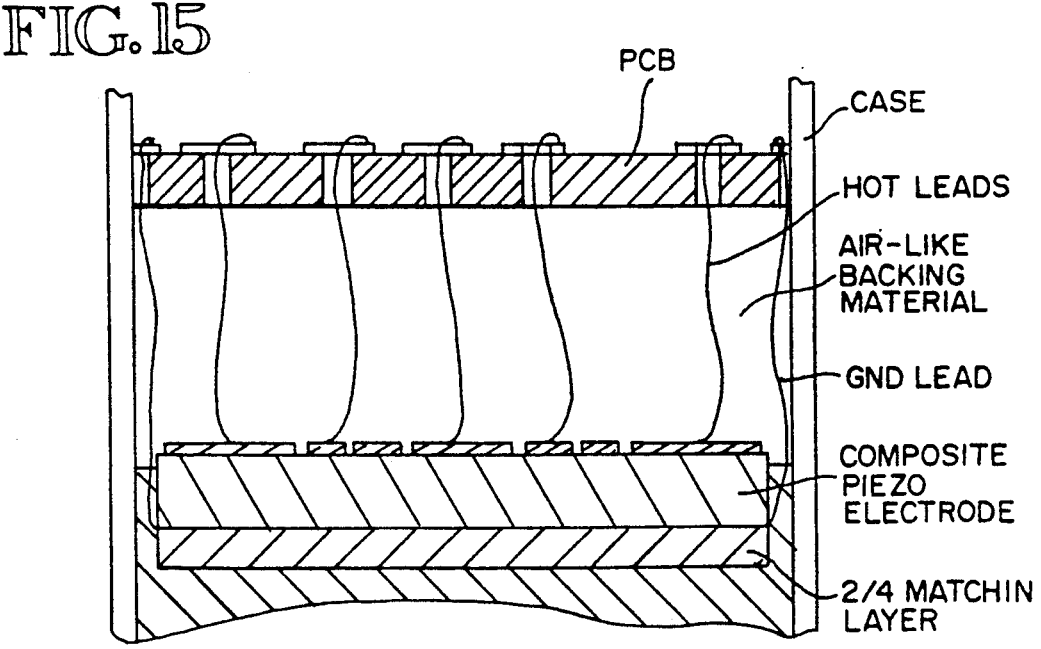

DOPPLER FLOW SENSING DEVICE AND METHOD FOR ITS USE

TECHNICAL FIELD

This invention relates to a Doppler flow sensor, and more particularly, to a Doppler flow sensor having an aiming capability for centering the flow sensor on the vessel carrying the flow.

BACKGROUND ART

This invention will facilitate the aiming of Doppler flowmeters which are based on the art described by Hottinger (in U.S. Pat. No. 4,431,936), Fu et al (in U.S. Pat. Nos. 4,067,236 and 4,519,260), and Skidmore et al (in U.S. Pat. No. 4,807,636). The flowmeters disclosed in these patents measure volume blood flow in biological vessels, such as the aorta. Such systems are to be distinguished from the clinical pre-ejection period (PEP) monitor disclosed by Rapoport et al, in the IEEE TRANSACTIONS OF BIOMEDICAL ENGINEERING, vol. BME-26, No. 6, June 1979. The system disclosed by Rapoport et al was useful in following the changing location of a fetal heart by means of continuous wave (CW) measurements of Doppler signals. However, it was incapable of precisely centering a Doppler sensor on a blood vessel.

One important application of a Doppler flowmeter is the measurement of cardiac output of a human heart. Another important application of a Doppler flowmeter or velocimeter is the measurement of the velocity of the blood flow from a human heart. The relevant anatomical details are shown in FIGS. 1A and 1B, which are respectively anterior and sagittal views of a human torso. These measurements are accomplished by measuring the forward blood flow in the ascending aorta 20, which emanates from the left ventricle of the heart (not shown) and is typically circular in cross section.

As shown in FIGS. 1A and 1B, the suprasternal notch 22 provides an acoustic window for the measurement of the blood flow in the ascending aorta 20. Simple pulsed wave and continuous wave Doppler devices such as ultrasonic transducer 24 located in the suprasternal notch 22 have been used to measure the integral of the systolic velocity of forward moving blood in the aorta. As can be seen from FIGS. 1A and 1B, the transducer 24 projects a beam 26 of ultrasonic energy which projects downwardly, substantially along the axis of the ascending aorta 20. When these measurements are combined with echo image measures of the aortic cross-sectional area, cardiac output can be calculated.

Simple Doppler velocimeters have not been routinely adopted as cardiac output devices for several reasons. Foremost, they cannot provide accurate flow measurements when they are not used in conjunction with an imaging device. In addition, trained ultrasonic personnel and suitable imaging equipment are not routinely available.

Simple velocimeters have suffered from several other theoretical drawbacks in their role as cardiac output devices. First, the velocity measurements that they make underestimate the true lumenal velocity as a function of the cosine of the angle of incidence of the ultrasonic beam relative to flow. Second, most commercially available devices generate beams which are not wide enough to uniformly insonify the breadth of the aortic lumen, with the consequence that uncertainty exists as to the relationship between the measured and true mean lumenal velocity. Third, clinicians have had difficulty in unambiguously aligning the Doppler sample volume with the center of the aorta. This has been a particularly troublesome aspect of continuous wave (CW) velocimeters, which create an axially large sample volume and, consequently, can easily interrogate arteries other than the aorta (particularly the innominate artery) from the suprasternal notch.

Clinical research has recently demonstrated the accuracy of a non-invasive cardiac output device which is based upon the attenuation compensated volume flowmeter (ACVF) principle first described by Hottinger. See, for example, *Determination of cardiac output in critically ill patients by dual beam doppler echocardiograph*, JACC, v. 13, No. 2, pp. 340-37, 1989, by Looyenga et al.

This device represents a major advance over the previously available Doppler cardiac output technology in that its measurements of flow can be made without an imaging device and are angle independent. Furthermore, when properly implemented, devices based upon this principle of operation do not suffer from the potential measurement errors due to non-uniform insonification of the aorta.

The device employs the annular array beam forming technology described by Fu and Gertzberg in ULTRASOUND IMAGING, 5, pp. 1-16 (1983). The Hottinger principle calls for the simultaneous generation of two overlapping Doppler sample volumes. A narrow sample volume must reside wholly within moving blood, while a wider sample volume must uniformly insonify a cross-sectional slice of the relevant biological vessel.

FIG. 2 is a schematic view of the interrogation profile of an ACVF device aimed at the aorta 20. The transducer 24 produces wide and narrow ultrasonic beams 26A and 26B. It has been known in the prior art to measure the cardiac output of the heart 28 through the ascending aorta 20 from measurements of the mean velocity V and the cross-section area A. The Doppler signal derived from the wide beam 26A is used to obtain a mean velocity estimate, and the ratio of the Doppler power present in the wide and narrow beams 26A and 26B is used to obtain an estimate of the projected aortic area. Multiplication of the two terms yields the instantaneous flow rate.

The primary impediment to the widescale commercial acceptance of such devices is the practical difficulty clinical personnel have in aligning the Doppler sample volumes with the aortic lumen. The criticality of the alignment process is accentuated by the fact that for various reasons (see below), the wide sample volume is often just large enough to uniformly insonify large aortas and the narrow sample volume is often just small enough to fit within the smallest aortic lumens. To our knowledge, no reliable criteria have been developed which unambiguously inform clinicians that Hottinger-type flowmeters are properly aligned relative to the aorta.

It has been suggested that maximization of the Doppler power in the wide and narrow sample volumes can serve as an adequate signature that the beams are acceptably centered about the aorta. FIGS. 4A-C are schematic representations of the wide and narrow power received as a function of sample volume position relative to the aorta. A sample volume position search will invariably be undertaken when operating with an apparatus as shown in FIG. 2. FIGS. 4A-C show that maximum wide and narrow power are achieved without fulfillment of the Hottinger requirements for sample volume placement, namely, uniform insonification of the aorta by the wide beam and placement of the narrow beam wholly within moving blood. The figures demonstrate that unless the acoustic search is thorough enough to bring the sample volumes through the center of the aorta, maximization of the wide and narrow powers may not be adequate criteria for sample volume localization.

It has also been suggested that maximization of the velocity in the narrow beam will result in adequate centering of the ACVF sample volumes in the aorta. The following discussion regarding the complex nature of the aortic velocity profile will serve to point out the limitations inherent in this approach.

FIG. 3 is a view of the blood flow velocity profiles expected in an aorta 30 and the left ventricular outflow tract 31 when no dilation of the ascending aorta is present. The aorta 30 is defined by a wall 32. The blood velocity profile at station 34 at the aortic orifice 33 is indicated by the array of arrows 36 which show the direction and magnitude of the velocity of the blood as a function of transverse position at station 34. The fact that the blood velocity at station 34 is substantially constant, even very close to the wall 32, is indicated by the series of parallel, equal-length arrows 32. The blood velocity profile at station 38, which is located downstream from station 34, is indicated by arrows 40. At station 38, the blood velocities nearest the wall 32 are lower than those in the center of the aorta 30, and, at the beginning of the aortic arch 46, the velocity is maximum near the inner curvature of the aorta 30. This skewing effect is seen even more clearly at station 42, where the innermost of the arrows 44 indicates that the maximum blood velocity is nearest the inner portion of the wall 32.

Because the portion of the aorta 30 in the aortic arch 46 is curved in two dimensions, the actual skew of the velocity profile may be complex. In addition, the branching of the arteries 48, 50, and 52 in this area to the arms and the head influences the blood velocity profile, especially at station 54. Further, wave reflections from these arterial branches will affect the blood velocity profiles near this portion of the ascending aorta.

The velocity profile skew is expected to change during systole, due to the different effects of blood acceleration and deceleration on the velocity profile. Another factor which complicates the flow of blood through the aorta is the transverse movement of the blood which occurs as the aortic wall 32 expands during systole. Because of the complicated nature of the blood flow in the aorta, it is clear that simple estimates of cardiac output, based, for example, on maximum velocity at a particular aortic station, can be very inaccurate.

Given the variability in human anatomy, it is difficult to predict whether a preset Doppler sample depth will reside at a level closer to station 34 or 42. If the Doppler sample volume resides at or near level 34, it may easily prove that the velocity gradient across the lumen is too slight to adequately distinguish the center of the lumen by maximization of narrow beam velocity, with the consequence that the wide beam may not be adequately centered. If, on the other hand, the sample depth occurs at or near station 42, manipulation of the transducer to achieve maximization of the velocity in the narrow beam will clearly place the sample volume to the side of the lumen. This could result in uneven insonification of the aorta by the wide beam, and possibly failure to place the narrow beam wholly within moving blood.

The invention provides a practical means for providing directional alignment information and confirmation that the Doppler sample volumes are acceptably centered about the aortic lumen during ACVF measurements. The invention also provides a practical and general means for providing directional alignment information for Doppler velocimeters.

DISCLOSURE OF THE INVENTION

It is an object of the present invention to provide Doppler power derived from each quadrant of the wide sample volume described in the Hottinger art as directional indicators to facilitate the proper alignment of the narrow and wide sample volumes relative to the biological lumen in which volume flow is to be measured.

It is another object of the present invention to provide an aiming mechanism for Doppler velocimeters.

It is a further object of the present invention to provide a device for non-invasive measurement of cardiac output.

This invention will be particularly useful as a pulsed Doppler sensor, operating at a frequency in the range of 2 to 4 MHz. It is expected that this invention will be particularly well-suited to be applied in a Hottinger-type, non-invasive cardiac output monitor. However, it may be suitable for use in other monitor types, as well.

According to one aspect, the invention is a device for measuring the velocity of a body fluid through a vessel at an interrogation depth in a body. The device comprises means for generating a pulsed transmitting signal having times of occurence, a first array of one or more ultrasonic transducers, and a second array of ultrasonic transducers. Each of the ultrasonic transducers in the first array is adapted to be driven by the pulsed transmitting signal to transmit pulses of ultrasonic energy into the body and to receive returning pulses of ultrasonic energy reflected within the body. The pulses of ultrasonic energy are transmitted with a desired directivity determined by the first array.

The second array of ultrasonic transducers is held in fixed positions relative to said first array. It is adapted to receive the returning pulses of ultrasonic energy from transverse directions relative to the desired directivity of the transmitted pulses.

The device further comprises detection means connected to said first and second arrays of ultrasonic transducers. The detection means is for receiving ultrasonic energy within time intervals which are respectively delayed from the times of occurrence of each of the pulsed transmitted signals by a period of time corresponding to the interrogation depth. The received ultrasonic energy is doppler-shifted by the velocity of the body fluid in the vessel. The detection means is also connected to the second array of ultrasonic transducers to generate a plurality of first received signals indicating the relative strengths of the received doppler-shifted energy in each transducer in the second array of ultrasonic transducers. The detection means is further connected to the first array of one or more transducers and receives the returning pulses of ultrasonic energy. The detection means measures the velocity of the fluid through the vessel at the interrogation depth from the returning pulses of ultrasonic energy.

According to another aspect, the invention is a device for locating the flow of a body fluid through a vessel at an interrogation depth in a body and measuring the volume of the flow through the vessel at that depth. The device comprises means for generating a pulsed transmitting signal and two arrays of ultrasonic transducers.

One of the arrays transmits pulses of ultrasonic energy into the body with a desired directivity. Each transducer in the first array is adapted to be driven by the pulsed transmitting signal to transmit pulses of ultrasonic energy into the body and also to receive the returning pulses of ultrasonic energy reflected from within the body. The other array of ultrasonic transducers is held in fixed positions relative to the first array and is adapted to receive the returning pulses of ultrasonic energy from transverse directions relative to the desired directivity of the transmitted pulses.

In addition, the device comprises detection means, connected to the two arrays, for receiving ultrasonic energy within time intervals which are respectively delayed from the times of occurrence of each of the pulsed transmitted signals by a period of time corresponding to the interrogation depth. The frequency of the received ultrasonic energy is Doppler-shifted by the velocity of the body fluid in the vessel. The detection means is connected to the second array of transducers to generate a plurality of first received signals indicating the relative strengths of the received Doppler-shifted energy received by each transducer in the second array. The detection means is further connected to the first array of transducers for producing one or more desired second received signals indicating the flow of the fluid through the vessel at the interrogation depth.

The device also includes direction indicator means for indicating a transverse direction to move the first and second arrays to optimally locate the vessel at the interrogation depth in the body. Finally, the device includes fluid volume indicator means for indicating the measured volume of body fluid passing through the vessel at the interrogation depth in the body.

According to a further aspect, the invention is a method for locating the flow of a body fluid through a vessel at an interrogation depth in a body and measuring the volume of the flow through the vessel at that depth. The method comprises the steps of providing first and second arrays of ultrasonic transducers and generating a pulsed transmitting signal having times of occurrence. The second array of ultrasonic transducers is held in fixed positions relative to the first array of ultrasonic transducers. The method further comprises the steps of driving each of the ultrasonic transducers in the first array by the pulsed transmitting signal to transmit pulses of ultrasonic energy into the body. The pulses of ultrasonic energy are transmitted with a desired directivity determined by the first array.

Further steps in the method are to receive returning pulses of ultrasonic energy reflected within the body, to receive the returning pulses of ultrasonic energy through the second array of ultrasonic transducers from transverse directions relative to the desired directivity of the transmitted pulses, and to receive ultrasonic energy from the second array of ultrasonic transducers within time intervals which are respectively delayed from the times of occurrence of each of the pulsed transmitted signals by a period of time corresponding to the interrogation depth. The received ultrasonic energy is doppler-shifted by the velocity of the body fluid in the vessel.

Additional steps in the method are to connect the detection means to the first array of transducers and to produce one or more desired second received signals indicating the flow of the fluid through the vessel at the interrogation depth, to generate a plurality of first received signals indicating the relative strengths of the received doppler-shifted energy in each transducer in the second array of ultrasonic transducers, and to indicate the measured volume of body fluid passing through the vessel at the interrogation depth in the body.

A transducer arrangement which will generate the narrow and wide sample volumes specified by Hottinger, and which will allow sampling of the Doppler power in each quadrant of the wide sample volume, and which is small enough to fit in the suprasternal notch of most adult subjects is described below.

BRIEF DESCRIPTION OF THE DRAWINGS

FIG. 11A is a graph of a trajectory of a large artery lumen across the center of the wide beam of the transducer array shown in FIGS. 5A-B.

FIG. 12B is a graph of the responses of the wide beam of the transducers shown in FIGS. 5A–B, as the small lumen follows the trajectory shown in FIG. 12A.

FIG. 12C is a graph of the response of the narrow beam of the transducers shown in FIGS. 5A–B, as the small artery lumen follows the trajectory shown in FIG. 12A.

FIG. 13 is a schematic diagram of one embodiment of a detection circuit for use in the ultrasonic sensor of the present invention.

FIG. 14 is a plan view of a second embodiment of an ultrasonic device in accordance with the present invention.

FIG. 15 is a elevation view of a third embodiment of the present invention.

Best Modes for Carrying Out the Invention

Figure 1A:
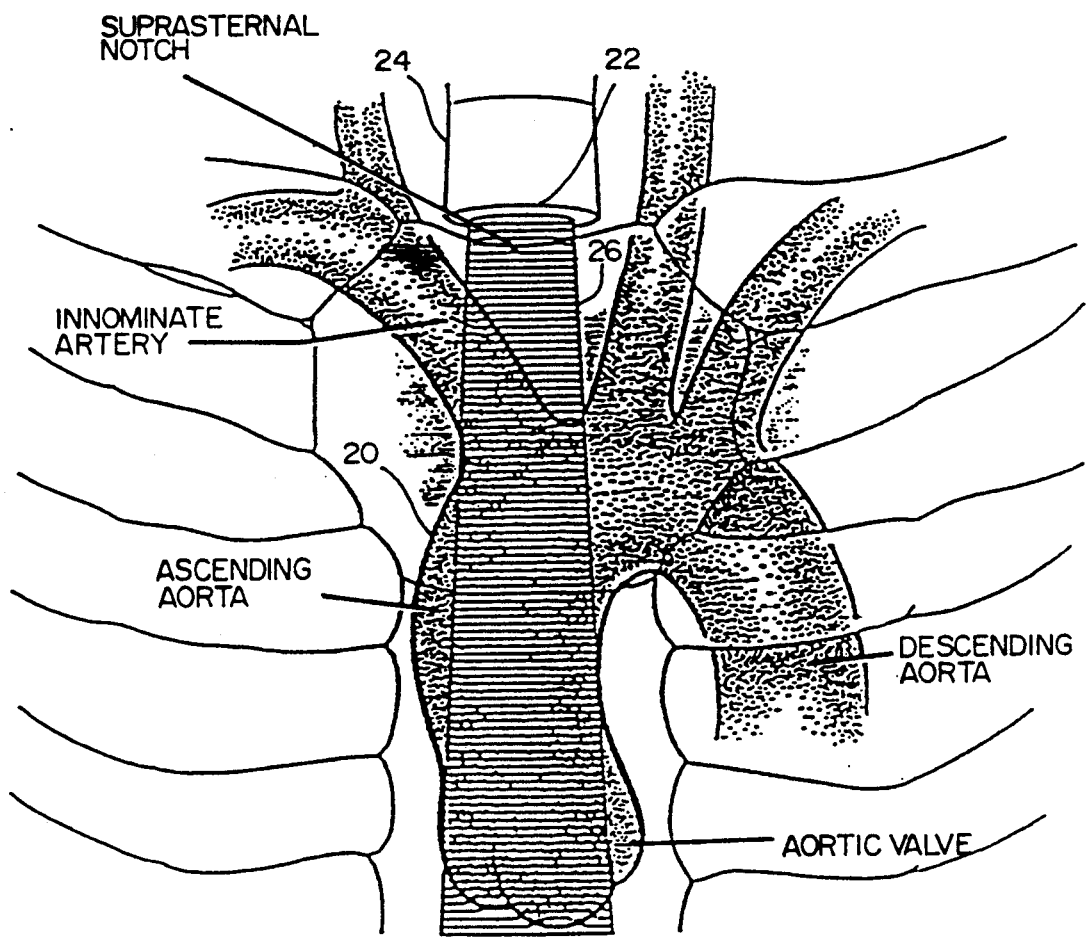
FIG. 1A is an anterior view of a human thorax.
Figure 1B:
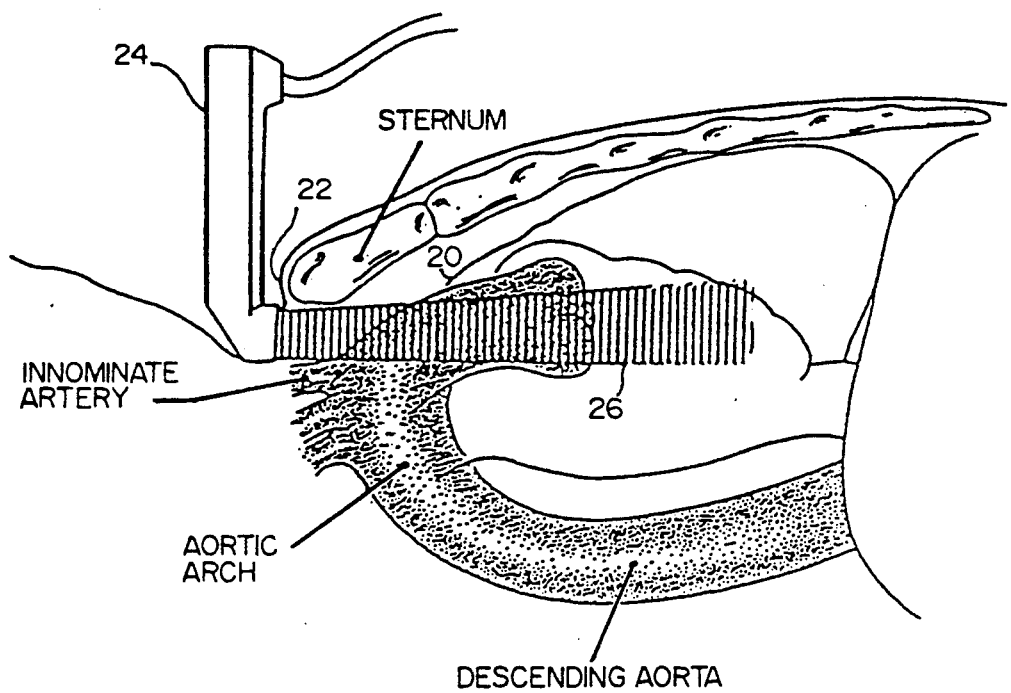
FIG. 1B is a sagittal view of a human thorax.
Figure 2:
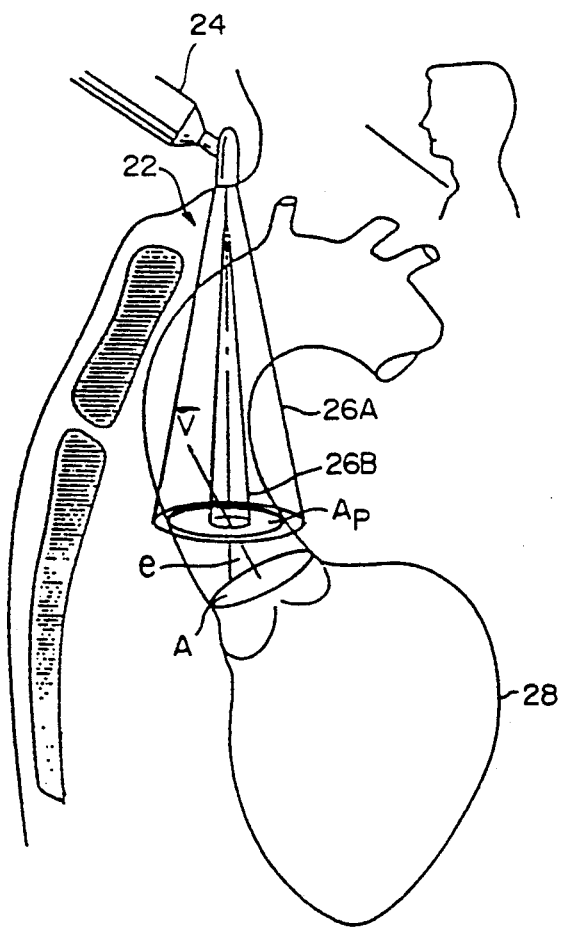
FIG. 2 is a schematic view of a typical insonification profile of an aorta with a sensor producing wide and narrow ultrasonic beams.
Figure 3:
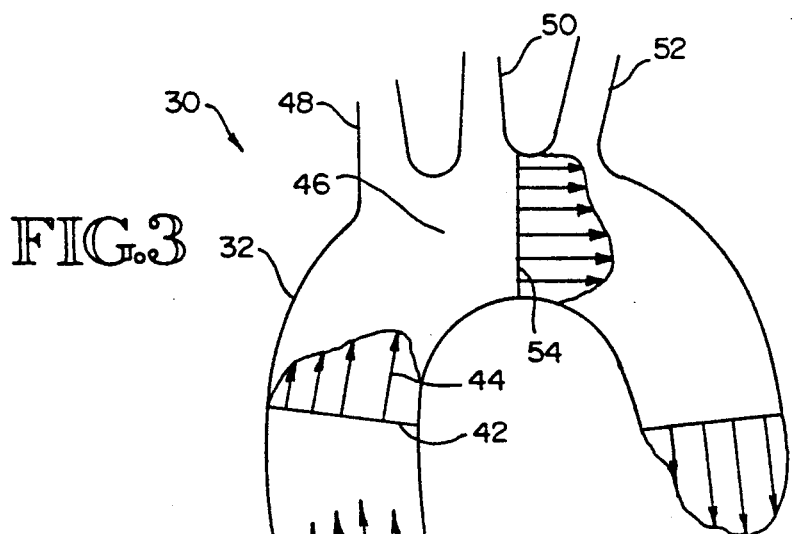
FIG. 3 is a view of the blood flow velocity profiles expected in the aorta when no dilation of the ascending aorta is present.
Figure 4A:
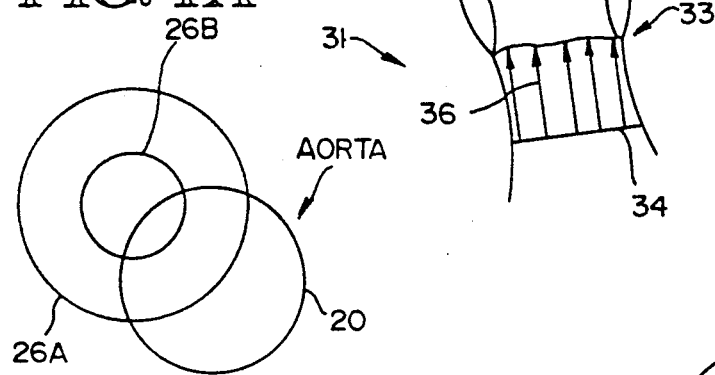
FIGS. 4A-C are schematic representations of various situations which can be encountered when operating with an apparatus as shown in FIG. 2.
Figure 4B:
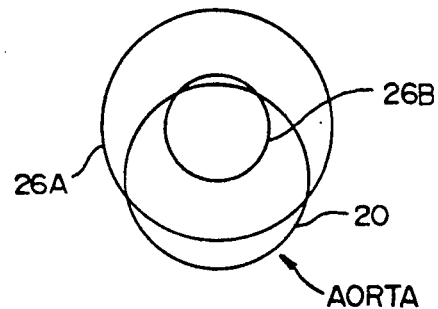
Figure 4C:
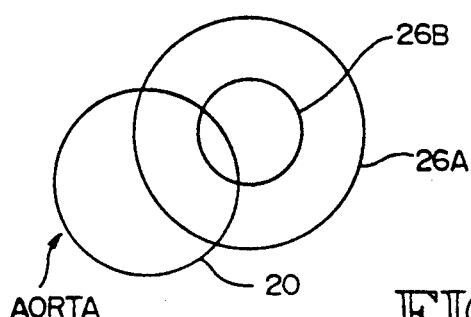
Figure 5A:
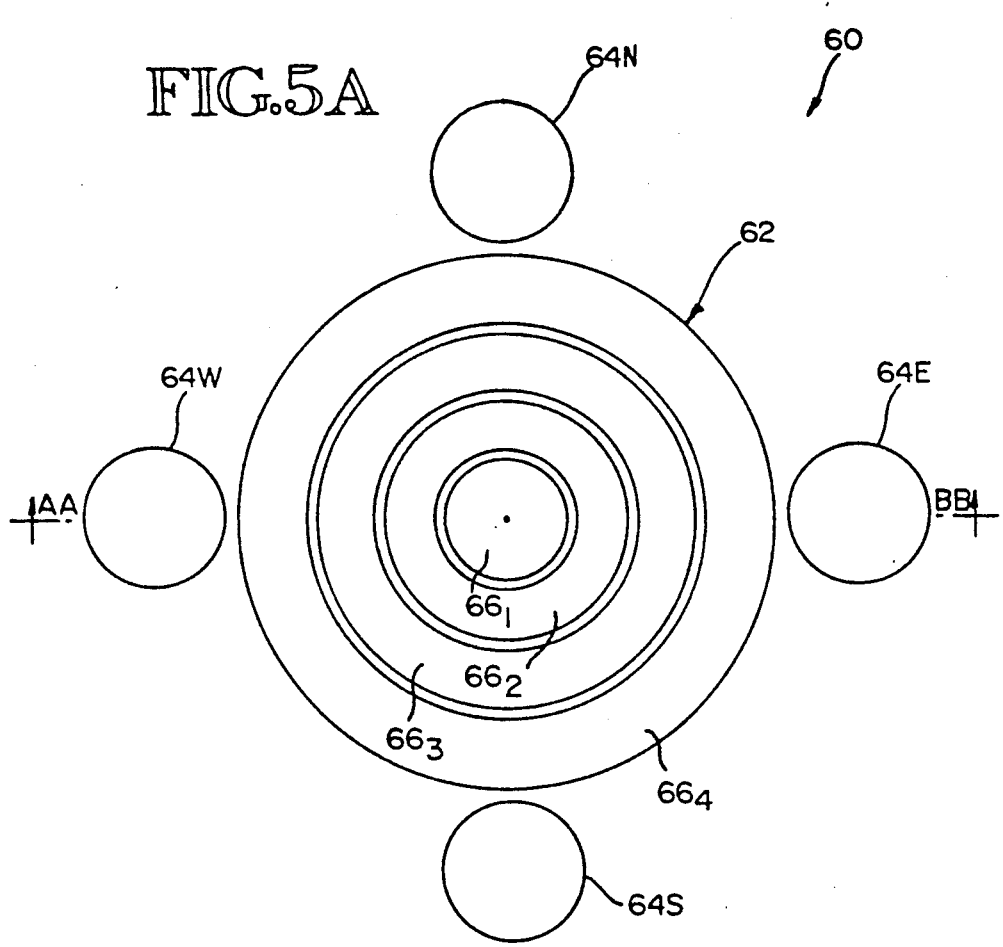
FIG. 5A is a plan view of a first embodiment of an ultrasonic transducer in accordance with the present invention.
Figure 5B:
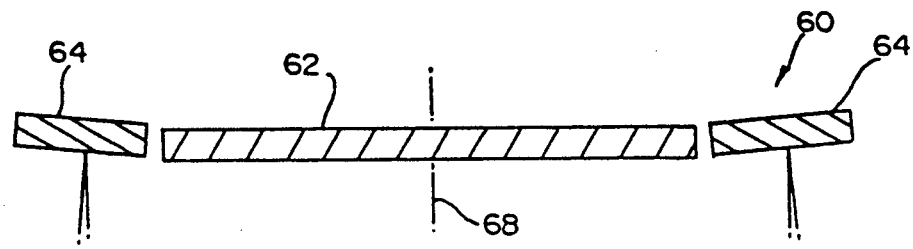
FIG. 5B is an elevation view of the first embodiment of an ultrasonic transducer in accordance with this invention, as shown in FIG. 5A, taken along either section lines AA or BB.

FIGS. 5A and 5B are a plan and an elevation view of a first embodiment of an ultrasonic transducer 60 which permits 1) the generation of the wide and narrow sample volumes specified in the Hottinger art, and 2) the independent sampling of Doppler power in each of four quadrants (designated, for convenience, as North, South, East and West) of the wide sample volume. The ultrasonic transducer 60 will be connected to an eight channel, pulsed Dopple acquisition and processing system (not shown) which will cause the ultrasonic transducer 60 to transmit a series of pulses and process the returning pulses. The eight channel system can be made according to principles wellknown by those skilled in the art. The transmitted pulses can consist of between five and fifteen cycles of a carrier frequency chosen from the range of 2 to 4 MHz at a pulse repetition frequency (PRF) of approximately 5 kHz to 40 kHz.

The ultrasonic transducer 60 will, in part, consist of a central four element annular array 62 which will be used to generate and receive the wide and narrow sample volumes described in the Hottinger art. The four circular ultrasonic transducers 64N, 64S, 64E, and 64W, which form a second array surrounding the central array 62 will be used to sense the Doppler power in each quadrant of the wide sample volume. Although the transducers 64N, 64S, 64E and 64W are shown to be 1.8 millimeter circles, they could also be any other convenient size or shape, such as annular segments, as is shown in a second embodiment of the device of the invention.

The central array 62 consists of four elements. Four concentric annular elements, designated $66_1$, $66_2$, $66_3$, and $66_4$, starting from the innermost element, are placed at the center of the central array 62. The diameter of the annular element $66_1$ is approximately 1.50 millimeters. The outside diameter of the annular element $66_2$ is approximately 3.20 millimeters, and is separated from the annular element $66_1$ by approximately 0.15 millimeter. The outside diameter of the annular element $66_3$ is approximately 4.90 millimeters, and is separated from the annular element $66_2$ by approximately 0.15 millimeter. The outside diameter of the annular element $66_4$ is approximately 7.00 millimeters, and is separated from the annular element $66_2$ by approximately 0.15 millimeter.

The circular transducers 64N, 64S, 64E, and 64W of the second array 64 are composed of a conventional piezocomposite material. Each of these elements is centered at a radius of 4.60 millimeters from the center of the central array 62 and has a diameter of 1.8 millimeters. As shown in FIG. 5B, which is taken along either section lines AA or BB of FIG. 5A, the central array 62 is substantially planar and perpendicular to an axis 68, while the transducers 64 in the second array are directed outwardly from the axis 68 at a small angle, such as five degrees. In this way, the ultrasonic fields received by each of the transducers 64 is further separated from the ultrasonic fields received by the other transducers 64 than it would otherwise be.

When using the annular array technology of Fu and Gertzberg in ACVF applications, the width of the wide beam is inversely related to the size of the inner element. In his thesis entitled *Measurement of Blood Flow Volume Rate by Doppler Ultrasound*, University of Bristol, 1987, Jonathan Evans discussed the width-to-thickness constraints imposed upon ultrasonic transducers constructed from standard piezoelectric materials. In the ACVF device fabricated by Evans, the properties of the piezoelectric material that he employed limited the minimum diameter of the central array element to two millimeters. This, in turn, resulted in a wide beam which provided a perfectly uniform pressure amplitude in a longitudinal interval of less than three centimeters at the six centimeter sample depth that he used. In terms of sensitivity to Doppler power, the wide beam was uniformly sensitive for a lateral distance of only two centimeters (many adults aortas are over three centimeters wide at a depth of six centimeters from the skin surface).

In order to escape from the width-to-thickness constraints descrbed by Evans, we have elected to fabricate our transducers out of diced, composite materials. We are thereby able to avoid lateral mode coupling effects and thereby make transducer elements of arbitrary size irrespective of carrier frequency. We are therefore able to produce wide beams which uniformly insonify the largest adult aortas (about 3.5 centimeters in diameter).

The elements of the transducer 60 are defined by an electrode pattern separated by shallow kerfs on the back surface of the piezocomposite material. The kerfs do not exceed 0.15 millimeter in width. Electrical tuning transformers (not shown), which are physically separate from the transducer 60, are respectively connected to each of the elements of the transducer 60. These transformers are used to separately drive each of the elements of the central array 62 to produce ultrasonic pulses and to separately receive the reflected pulses. The piezocomposite material can advisably include either quarter-wave matching layers and/or air or air-like backing materials in order to maximize the sensitivity of the transducer 60. The transducer 60 is connected to a conventional handle designed for good access to the suprasternal notch, and appropriate coaxial cables are used to transfer signals to and from the transducer 60. The assembly including the device 60 and the handle are made from materials which are unaffected by indefinite immersion (at least 350 hours) in water and aqueous coupling gels at a temperature of 65 Celsius.

Figure 6A:
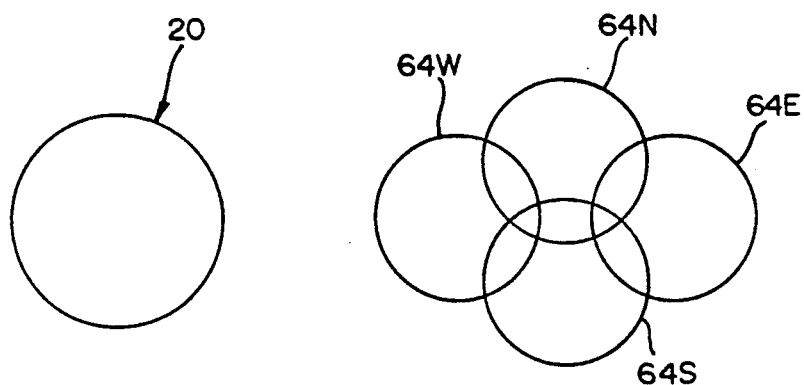
FIGS. 6A-C are schematic representations of three stages of the operation of centering the first embodiment of the present invention on an aorta.
Figure 6B:
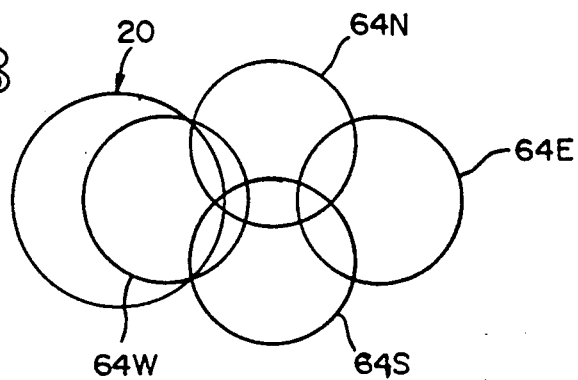
Figure 6C:
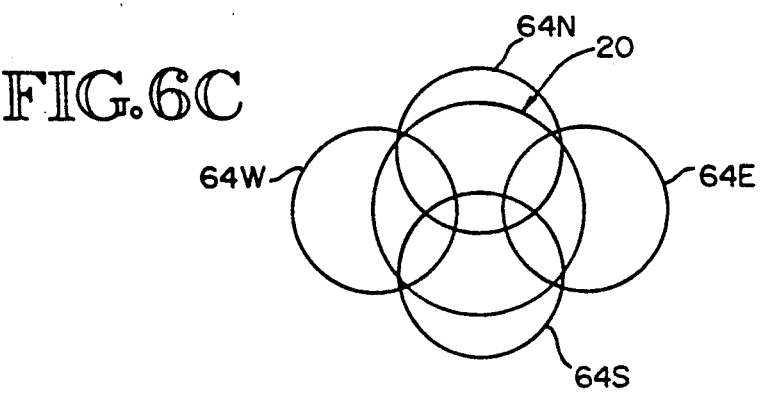

FIGS. 6A–C are schematic representations of three stages of the operation of centering an embodiment of the present invention on an aorta 20. FIG. 6A shows the overlapping direction fields corresponding to the four elements of the second array 64 when they are separated from the aorta 20. In this position, none of the transducers in the array 64 will be receiving any Doppler power attributable to forward blood flow from the aorta 20. As depicted in FIG. 6B, element 64W will receive the most Doppler power. Elements 64N and 64S will receive a lesser, but equal, amount of Doppler power. Element 64E will not receive any Doppler power. This distribution of Doppler power indicates that the fields of the array 64 should be shifted to the left. Shifting the fields of array 64 to the left will also result in the shifting of the fields of first array 62, since arrays 62 and 64 are held in fixed positions relative to one another. Finally, in FIG. 6C, each of the elements in the array 64 will receive the same Doppler power, indicating that the fields of the arrays 62 and 64 are centered on the aorta 20.

Generation and Reception of the Wide Sample Volume

Figure 7A:
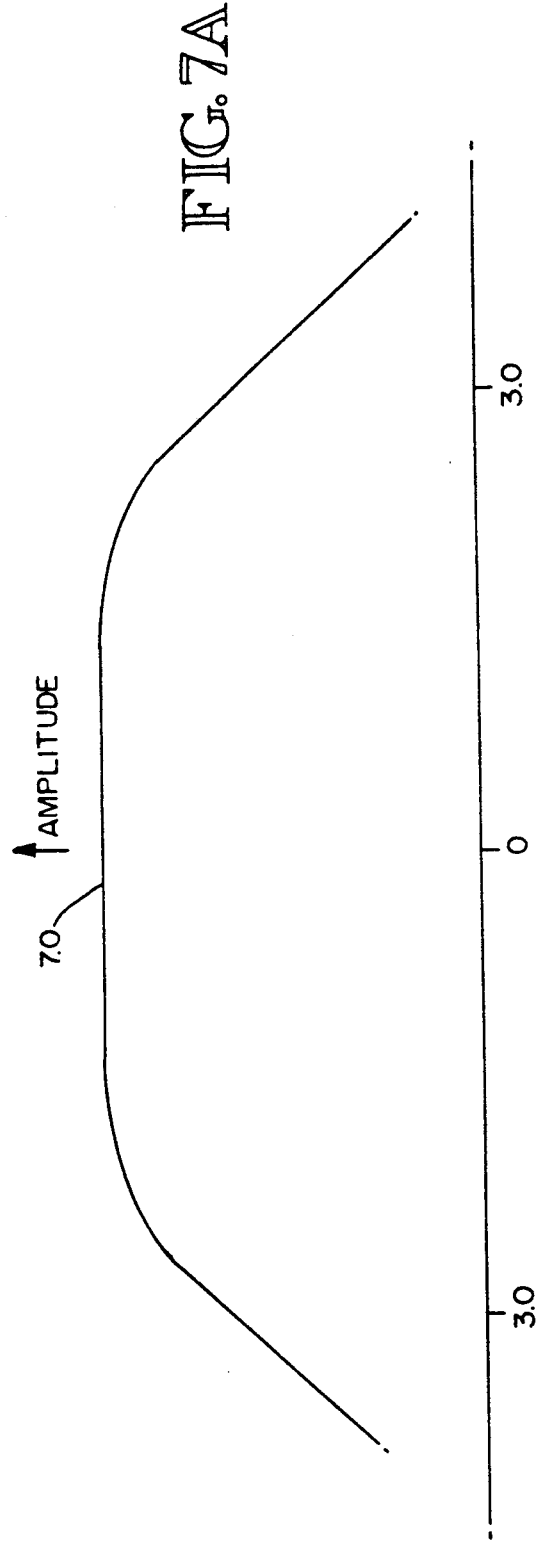
FIG. 7A is a plot of the acoustic amplitude of the wide beam of the ultrasonic sensor of FIGS. 5A-B, as a function of transverse distance.
Figure 7B:
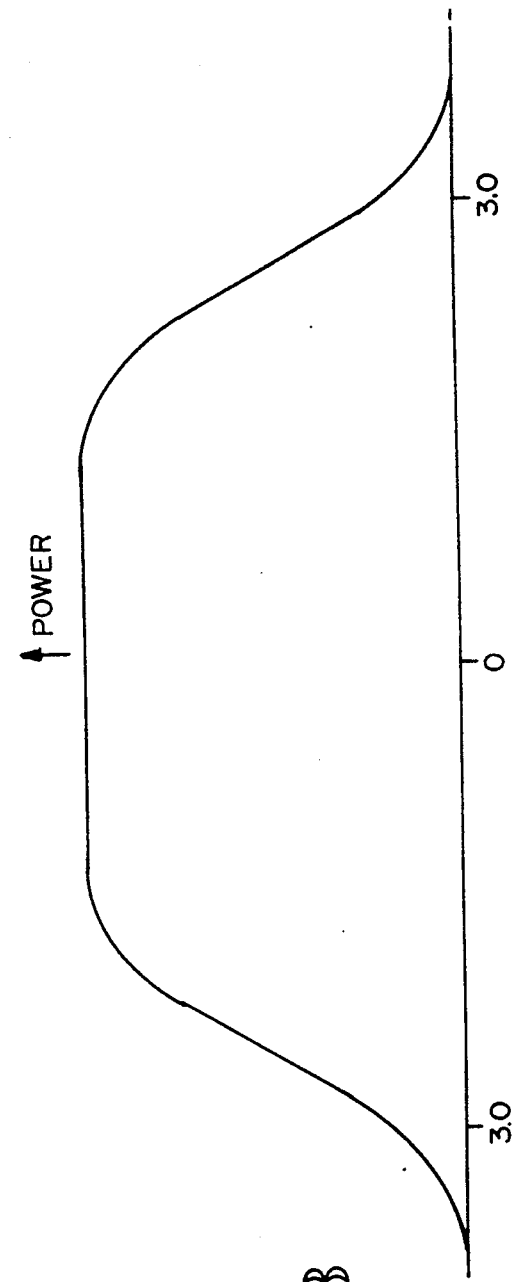
FIG. 7B is a plot of the lateral sensitivity to Doppler power of the ultrasonic sensor of FIGS. 5A-B, as a function of transverse distance.

The sequential array elements are driven simultaneously and out of phase with one another, with variable gain weightings, to generate a uniform wide beam in the far field of the transducer. FIG. 7A is a plot of the acoustic amplitude, as a function of transverse distance, of the wide beam generated by the transducer depicted in FIGS. 5A-B when it is driven at 2 MHz and sampled at a depth of seven centimeters. At this point the wide beam has an approximately constant amplitude 70 over a transverse distance of approximately four centimeters, which is large enough to uniformly insonify the largest aortas commonly encountered in adult subjects. The radiation pattern depicted in FIG. 7A is produced by using the gain and phase settings noted in Table 1. After a suitable time delay (consonant with a seven centimeter sample depth), the Doppler signals received by the inner three elements of the central array 62 will be summed (using the same phase and gain setting as described in Table 1) to permit the calculation of the total Doppler power and mean velocity of blood in the wide sample volume. FIG. 7B is a plot of the wide beam's lateral sensitivity to Doppler power at a seven centimeter sample depth.

TABLE 1

| Element | Gain | Phase(degrees) |
|---------|-------|----------------|
| 1 | 1.000 | 0 |
| 2 | 0.095 | 180 |
| 3 | 0.010 | 0 |
| 4 | 0.000 | — |

In spite of our ability to make efficient transducers of arbitrary size, several practical limitations on wide beam size persist. First, while it is necessary to make the wide sample volume wide enough to uniformly insonify the largest aortas that we anticipate encountering, it is disadvantageous to make the wide sample volume so large as 1) to insonify adjacent arterial lumens such as the pulmonary artery, and 2) to increase the likelihood of troublesome reflections off structures such as the trachea and lungs.

The avoidance of measurement errors due to contamination of the aortic flow signal by Doppler signals from forward moving blood in the pulmonary artery was a major consideration in the operational design of our device. Preliminary experiments with magnetic resonance imaging (MRI) and Doppler have indicated that in most subjects, it is possible to make virtually uncontaminated aortic blood flow measurements. At preferred sample depths (five to seven centimeters for small adult subjects, and six to eight centimeters for large adults), the Doppler sample volume is generally above the main pulmonary artery trunk which runs parallel to the aorta. At these depths, the Doppler sample volume tends to be contiguous with the transversely oriented, right and left pulmonary artery branches. While there may be, in some subjects, a small upward (toward the transducer) movement of blood in the right and left pulmonary branches, the high angle of incidence of this flow relative to the ultrasonic beam generally results in small Doppler shifts which are removed by the wall filter (high-pass) circuitry. Finite amounts of contamination can occur however, and it is obviously desirable to minimize the insonification of the pulmonary artery.

Another disadvantage of increasing the wide beamwidth beyond the size of the aorta is that this results in a lowering of the ultrasonic intensity (expressed as a percentage of input energy) in the aorta, and thereby a reduction in the signal-to-noise ratio of our device. If, in an attempt to maintain the signal to noise ratio, it is necessary to raise the input energy imposed upon the inner element to compensate for increased beam width, there is the very real risk of exceeding the regulatory limitations placed upon maximum ultrasonic intensity (expressed in watts/centimeters$^2$). This is especially true as the size of the inner transducer element is progressively minimized, as is the skin contact area of the inner element, in order to make progressively wider beams.

When making ACVF measurements on the largest aortas, the practical limitation imposed on the wide beamwidth demands that the operator be able to precisely center the Doppler sample volumes about the aorta.

Generation and Reception of the Narrow Sample Volume

In order to maximize the pulse repetition frequency of the Doppler system, the narrow sample volume will not generally be transmitted and received independently of the wide sample volume, even though in many cases it is possible to do this without violating the aliasing criteria, which determines a lower limit to the pulse repetition frequency.

Figure 8:
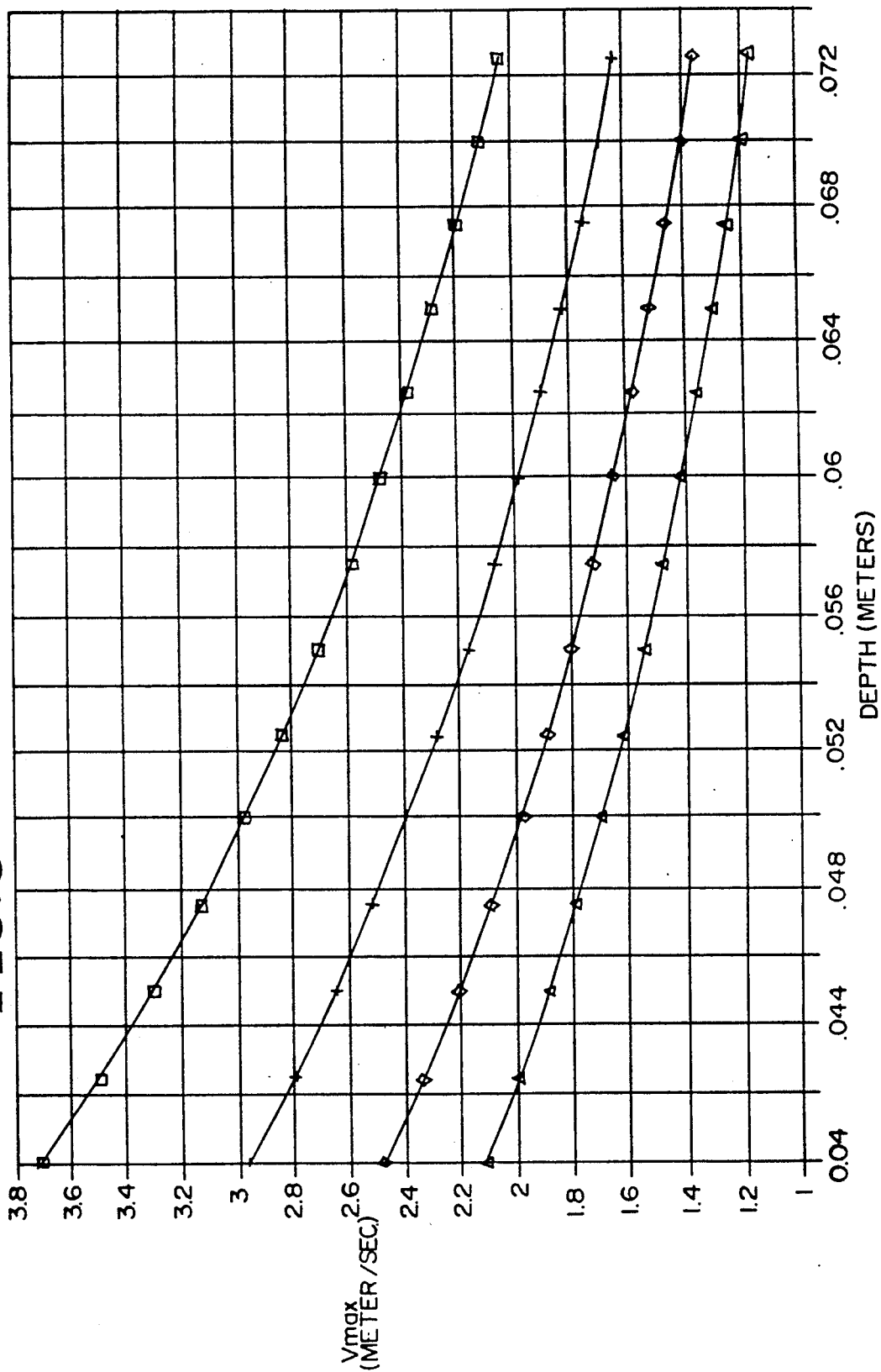
FIG. 8 is a graph of the relationship between sample depth and carrier frequency versus maximum measurable blood velocity for a pulsed Doppler system in human tissue.

FIG. 8 shows the relationship between sample depth and carrier frequency versus maximum measurable blood velocity for a bidirectional pulsed Doppler system in human tissue. FIG. 8 shows that at 2 MHz and a sample depth of six centimeters, it is possible to comfortably measure the anticipated maximum aortic velocities (1-1.5 m/sec). Halving the effective pulse repetition frequency to accommodate independent transmission and reception of the wide and narrow beams would halve the maximum velocity that could be tracked (in the wide or narrow beam) at any given interrogation depth. It is very likely that with a 2 MHz Doppler and a sample depth of 5 centimeters, it is possible to transmit the wide and narrow beams independently and still be able to track the maximum aortic velocity without violating the Nyquist aliasing criteria.

Following transmission of the uniform, wide beam, as discussed in connection with FIG. 7A, the range-gated Doppler signals received by each receive transducer 64 and element 66 will be summed, with variable gain and equal phase, to effectively generate a narrow Doppler sample volume as described in the Skidmore patent. The settings to produce the wide beam are different from those required to produce the narrow beam. Further, as described in the Hottinger art, the Doppler power ascribable to this narrow sample volume is calculated in order to compensate for variable inter-subject ultrasonic attenuation and scattering in order to derive an accurate projected aortic area.

When using the Fu/Gertzberg annular array technology, narrow beam size is inversely related to the diameter of the annular array. Many small subjects, who possess accordingly small aortas, may not be able to tolerate suprasternal transducers with footprints in excess of twelve millimeters. An additional constraint which limits the narrowness of the inner sample volume (given a fixed transducer footprint) is that aliasing considerations may, under some circumstances, preclude the independent transmission and reception of the wide and narrow sample volumes. As a consequence of these two factors, the beamwidth (mainlobe) of the narrow sample volume may be in excess of one centimeter at a six centimeter sample depth.

Given the size of the narrow sample volumes that can be achieved, small (0.5 centimeter) misalignments of the narrow beam relative to the center of small aortic lumens (two centimeters diameter), will result in underestimation of narrow power, and hence erroneous estimates of aortic area and cardiac output. (When dealing with the smallest aortas, the wide beam tolerance for misalignment generally exceeds that of the narrow beam).

Optimization of the Sample Depth

In ACVF applications, the ability to pick a sample depth with minimum angle of incidence and hence minimum projected cross-sectional area is important given the constraints on wide beam formation enunciated above. Similarly, when using a pulsed, wide-beam Doppler to obtain an accurate mean velocity estimate for flow in a vessel, minimization of the angle of incidence and the concomitant underestimation of means velocity is obviously a desirable goal.

Figure 10A:
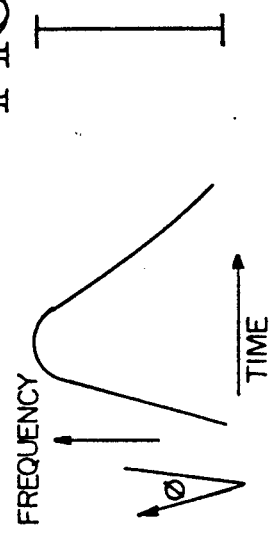
FIGS. 10A-C are respectively graphs of the expected spectral responses obtained in Doppler frequency measurements made in the three situations depicted in FIG. 9.
Figure 10B:
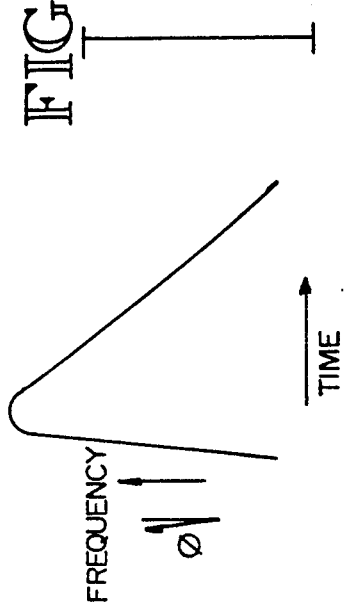
Figure 10C:
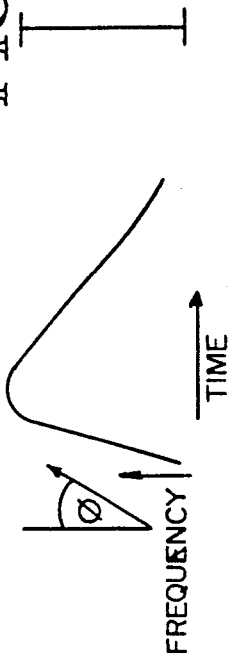
Figure 9:
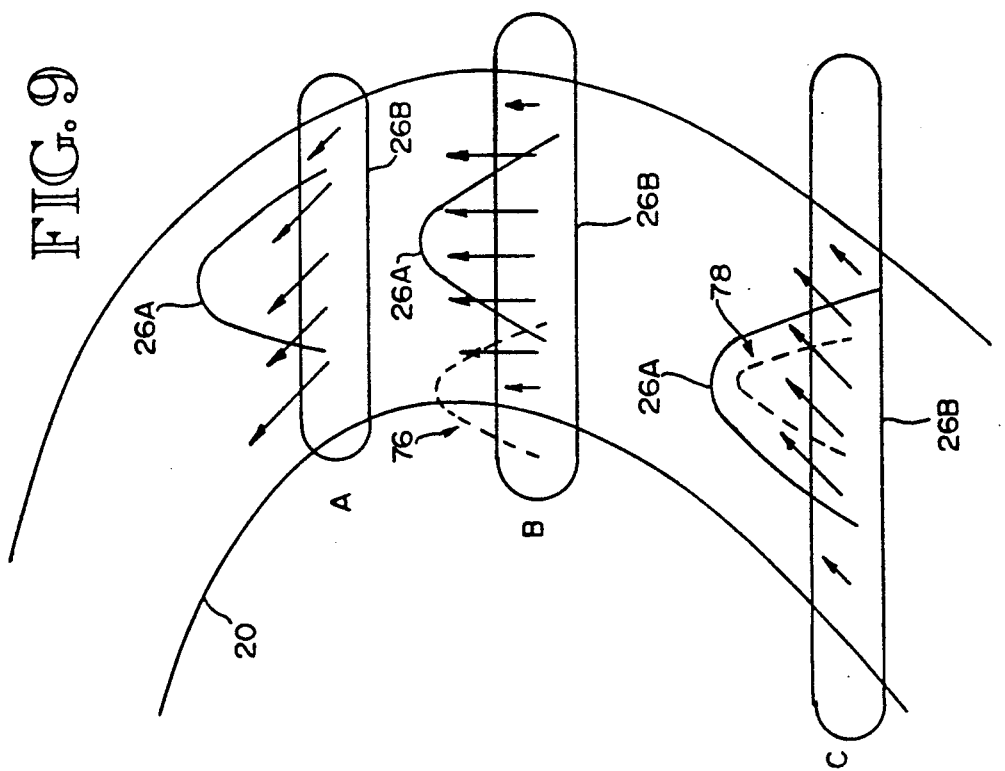
FIG. 9 is a schematic diagram of three situations under which measurements may be made in accordance with the present invention.

FIG. 9 and 10A-C show how analysis of the spectral characteristics of the wide and/or narrow beam may help in the optimization of the sample depth chosen for a subject. FIG. 9 shows three possible measurement locations A, B, and C. FIGS. 10A-C are schematic representations of the Doppler spectra corresponding to these positions. FIGS. 10A-C show that the narrow and wide spectra are narrowest and contain the highest velocities at a depth at which the angle of incidence comes closest to zero degrees.

Inspection of FIG. 9 reveals that the accuracy of this optimization method is dependent upon being able to reliably center the wide sample volume(s) relative to the aortic lumen. If, for instance, in an ACVF application, the narrow sample volume at level B was placed at the side of the aortic lumen (as indicated by reference numeral 76), whereas it was centered (as indicated by reference number 78) at level C, comparisons of the velocities at these two depths might mislead an operator into believing that the angle of incidence $\theta$ was greater at level B.

Generation and Receipt of Quadrant Doppler Information

Referring again to FIGS. 5A-B, as is used to produce the narrow sample volume, the Doppler quadrants in 64 will only be received. An outward cant of the annular transducers 64 (discussed subsequently) will afford greater separation of the fields produced by the 1.8 millimeter discs. The precise geometry of the aiming field angular displacement can be empirically determined for each transducer configuration to maximize the effectiveness of the aiming guides.

Figure 11B:
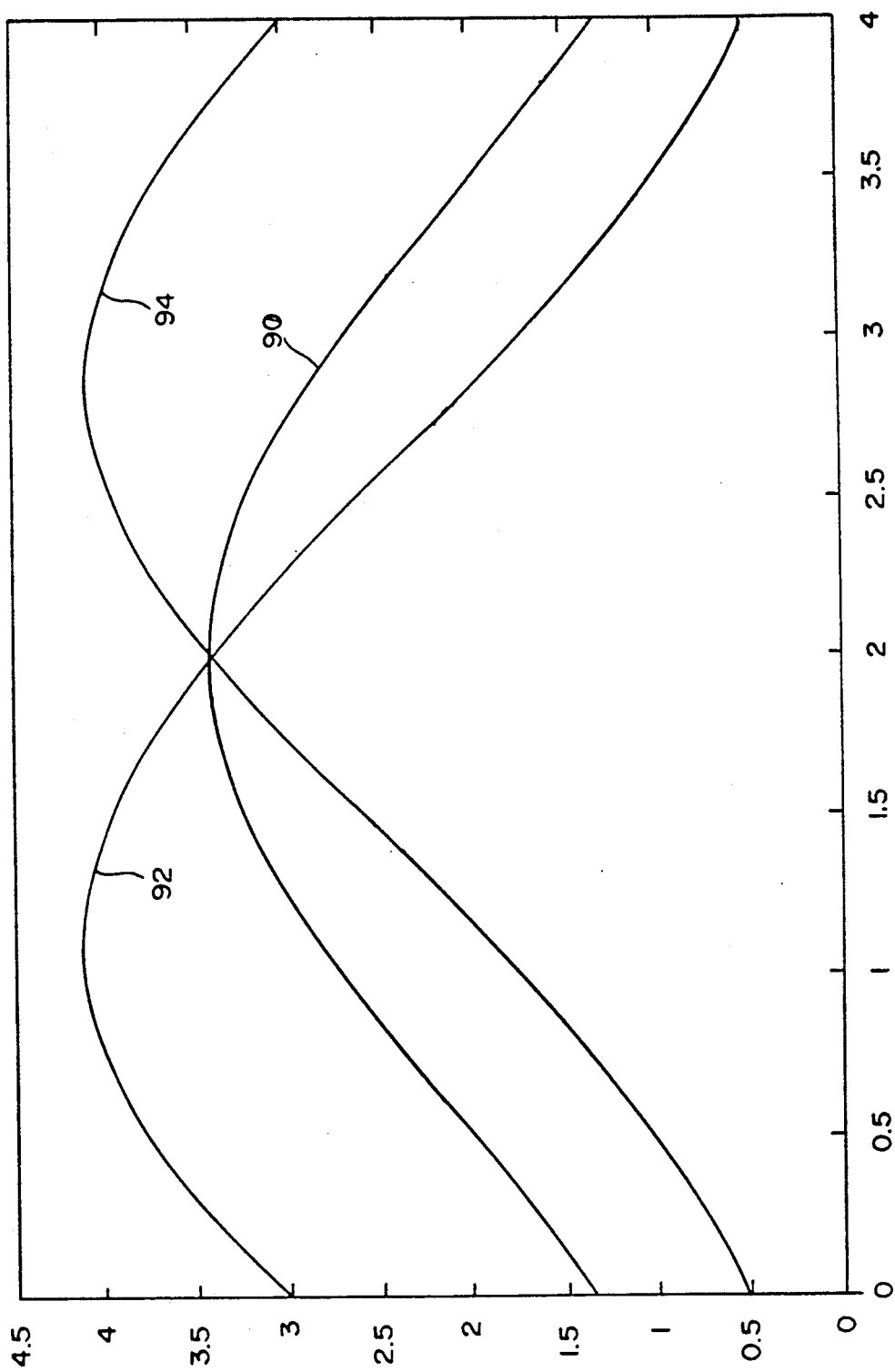
FIG. 11B is a graph of the responses of the wide beam of the transducers shown in FIGS. 5A-B, as the large artery lumen follows the trajectory shown in FIG. 11A.
Figure 11C:
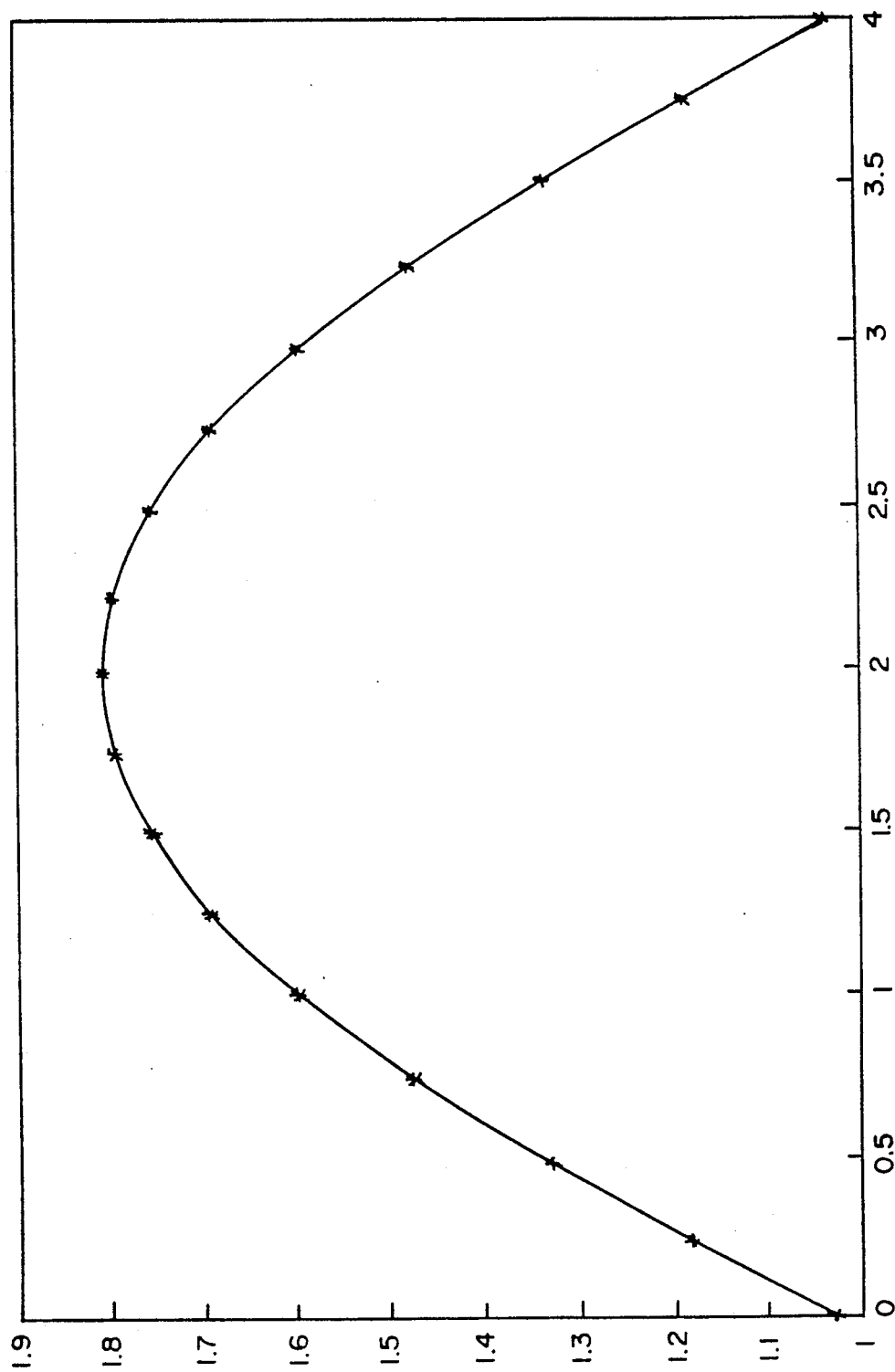
FIG. 11C is a graph of the response of the narrow beam of the transducers shown in FIGS. 5A-B, as the large artery lumen follows the trajectory shown in FIG. 11A.
Figure 11D:
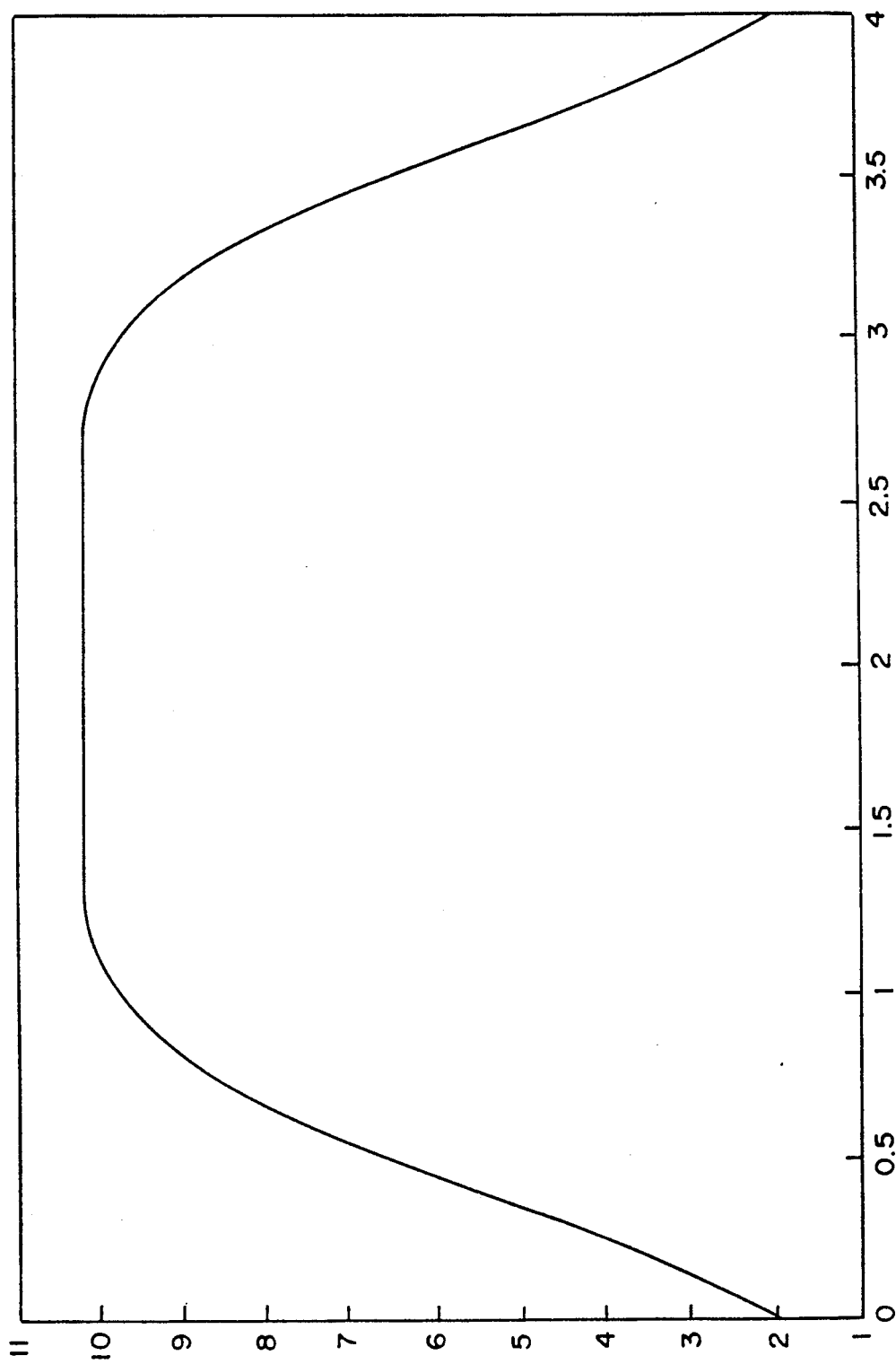
FIG. 11D is a graph of the responses of the directional elements of the transducer array shown in FIGS. 5A-B, as the large artery lumen follows the trajectory shown in FIG. 11A.
Figure 12A:
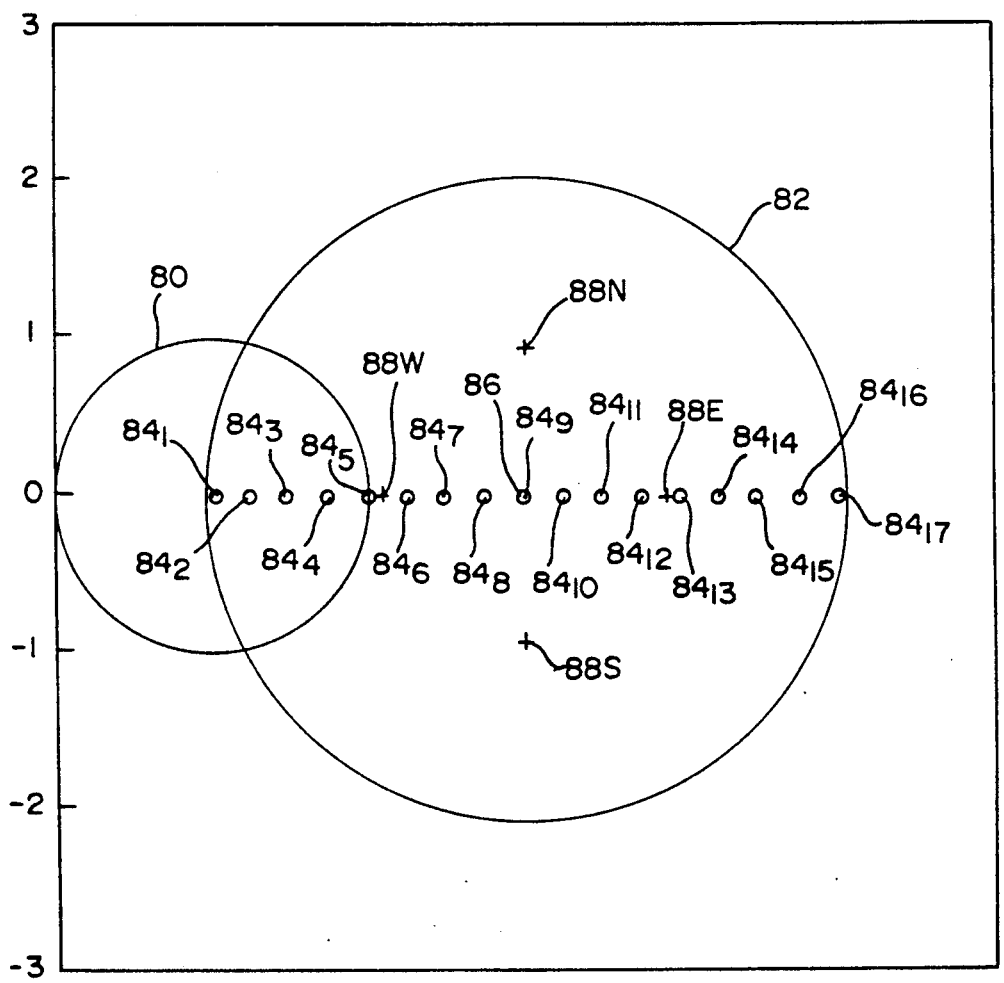
FIG. 12A is a graph of a trajectory of a small artery lumen across the center of the wide beam of the transducer array shown in FIGS. 5A–B.
Figure 12D:
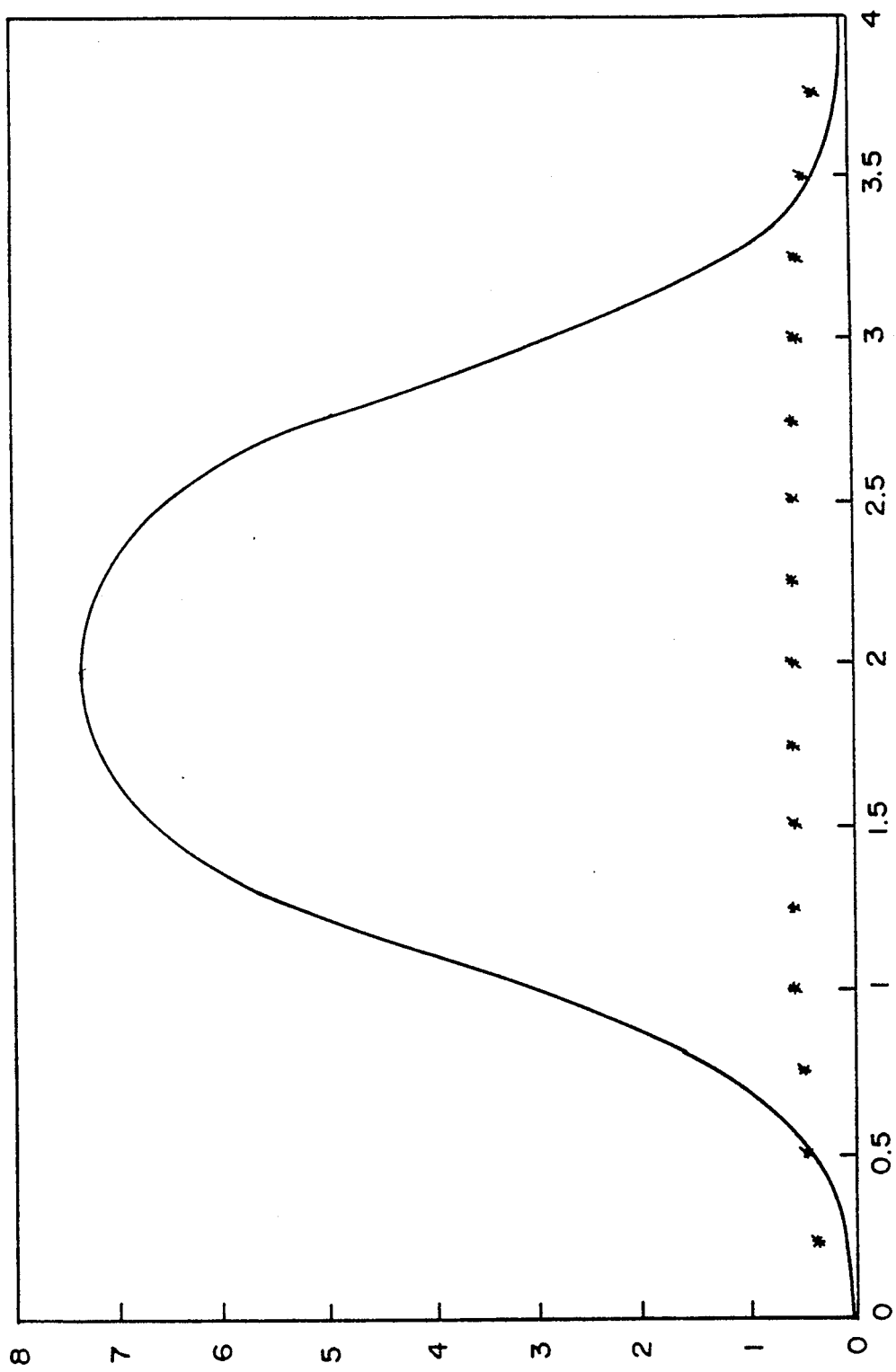
FIG. 12D is a graph of the responses of the directional elements of the transducer array shown in FIGS. 5A–B, as the narrow artery lumen follows the trajectory shown in FIG. 12A.

In practice it is necessary to limit the size of the wide beam to that of the largest anticipated aortas. This, in turn, places added importance on centering the wide beam in large aortas, as the theory of operation of ACVF devices calls for uniform insonification of the target lumen. FIGS. 11A-C show the effects of beam misalignment on the calculation of total wide beam power when measurements are made on a large (35 millimeters diameter) aorta. In the situation depicted, the flat portion of the wide beam is just barely wide enough to uniformly insonifiy the very large aorta depicted in the figure. The wide power is perceptively diminished with very small beam misalignments. FIGS. 11A-D also show that, on a percentage basis, the narrow beam power is less sensitive to small misalignments. The consequence of wide beam misalignment in this instance is twofold. First, the wide-to-narrow power ratio is altered, with the resultant error in the estimate of projected aortic area. Second, the aorta is not uniformly insonified and errors in the estimate of mean velocity can occur.

More specifically, FIG. 11A is a graph of a trajectory of an artery lumen 80 across the center of the wide beam 82 of the transducer array 60 shown in FIGS. 5A-B. The interrogation depth is seven centimeters, and the width of the aorta is 3.5 centimeters. The graph is centered on the position of the wide beam 82, and the trajectory of center of the artery lumen 80 is indicated by the series of small circles $84_1$ through $84_{17}$. The trajectory 84 passes through the center 86 of the wide beam 82. The positions of the centers of the aiming guide fields produced by the aiming transducers $64_N$, $64_S$, $64_E$, and $64_W$ at this depth are indicated by the respective crosses $88_N$, $88_S$, $88_E$, and $88_W$.

FIG. 11B is a graph of the responses of the directional elements of the array shown in FIGS. 5A-B, as the artery lumen follows the trajectory 84 shown in FIG. 11A. If the wide beam depicted in FIG. 11A is generated during the transmit cycle, the Doppler power fields received from the transducers 64 will vary as a function of aortic position. Curve 90 shows the variation of the relative power scattered from the aorta toward either of the transducers $64_N$ and $64_S$, which are transverse to the direction of the trajectory 84. Curves 92 and 94 respectively show relative Doppler power scattered from the aorta in directions of the transducers $64_W$ and $64_E$.

The relative Doppler power scattered toward the transducers $64_W$ and $64_E$ reaches maximums at different points along the trajectory specified by points 84 (in FIG. 11A). The relative Doppler power scattered toward transducer $64_W$ reaches a maximum before the device 60 is centered on the aorta 80, while the relative power scattered toward transducer $64_E$ reaches a maximum after the device 60 is centered on the aorta 80. Equalization of the Doppler power returns from each aiming guide transducer 64 will occur only when the wide sample volume is centered about the aorta 80. It is only at this point that the Doppler power received through the wide beam is maximized. Therefore, the differences between the Doppler power returns from diametrically opposed transducers 64 can be used to specify the direction and, to some extent, the distance that the device 60 must be moved to center it over the aorta that is being measured.

FIGS. 12A-D are analogous to FIGS. 11A-D except that they depict a situation in which the wide and narrow beams are brought into various stages of alignment with a small aorta (two centimeter diameter) at a sample depth of six centimeters. The FIGURES show that narrow power is noticeably diminished with small amounts of beam misalignment whereas the wide beam's tolerance for misalignment is greater. The FIGURES also show that the Doppler power differences in the aiming guide quadrants would be sufficiently great to alert the operator that significant beam misalignment has occurred.

The inventive device can make use of independent spectral analysis of subsections of the wide sample volume. If one makes the Hottinger assumption that uniform ultrasonic backscattering characteristics occur throughout the aortic lumen, the wide and narrow sample volumes should be centered about the aortic lumen when the Doppler power generated by forward moving blood is equivalent in each quadrant of the wide beam. In order to remove low velocity signals emanating from vessel walls or the pulmonary artery, appropriate velocity thresholds will be imposed upon the quadrant power calculations. If the power in each quadrant is not equal, the differences in power can provide directional alignment information to the operator on a heartbeat-to-heartbeat basis. The differences in Doppler power seen in the quadrants will be quite pronounced when the wide and narrow sample volumes are significantly misaligned relative to the aorta.

The theory of operation of the invention calls for discrimination of forward and reverse velocity, as arteries and veins which are characterized by directionally opposed flow patterns often lie adjacent to one another. For instance, the superior vena cava runs parallel to the aorta at the sample depths that we employ. Flow in this lumen is directionally opposed to aortic flow, except in the presence of tricuspid regurgitation. We may in fact be able to interpret the presence of a dominant vena caval flow signature in any of the quadrants as an indication that our wide beam is significantly misaligned relative to the aorta.

An additional assumption of ACVF devices is that the acoustic environment through which the wide and narrow beams must pass is homogeneous enough to permit relatively distortion-free beam formation. It is also assumed that the ultrasonic scattering properties of blood are uniform throughout the acoustic cross-sectional slice. These assumptions have not been tested directly in-vivo, although the excellent clinical results reported by Looyenga inferentially argue that beam distortion and non-uniform scattering are not major problems in most subjects.

Significant problems in this regard may occasionally occur, however. The invention described herein could provide a warning to the operator that uniform insonification of the aorta and/or uniform scattering are not occurring. If, for instance, the operator was ultimately unable to achieve equalization of the power in each quadrant despite repeated repositionings of the transducer, he or she might be able to infer that either the insonification of the aorta was uneven, or that the scattering properties within the aorta were not uniform.

The theory of operation of the invention may also be violated if the shape of the target lumen deviates significantly from that of a circle. Preliminary MRI data that we have obtained, however, indicates that most aortas are essentially circular. Also, the intersection of the Doppler sample volume with the aortic lumen will differ from being perfectly circular and will tend towards an elliptical shape as the angle of incidence increases. Our anatomic data indicate that, in most cases, the angle of incidence is not more than thirty degrees. Simulations of this situation reveals, however, that the present aiming guide scheme will still work, since virtual equalization of the Doppler power in each quadrant of the wide beam still occurs when the wide beam is centered about the aorta. It is significant, however, that despite finite angles of incidence this transducer array accomplishes uniform insonification for virtually all adult aortas.

Circuit Description

FIG. 13 is a schematic diagram of one embodiment of a transmit and detection circuit 100 for use in the ultrasonic sensor of the present invention. Circuit 100 can cause the device 60 to transmit appropriate pulsed signals through the first array 62. Circuit 100 can also process the received transducer signals and produce both wide and narrow receive Doppler signals. Further, circuit 100 can produce signals indicating the relative power and velocities measured by the aiming transducers 64 in order to specify the direction in which the device 60 should be moved in order to be optimally placed with respect to the aorta.

The device 60 is connected to the circuit 100 through a connector 102 which permits the ready replacement of one embodiment of the device 60 for another. The circuit 100 consists of a transmitter section 104, receiver circuitry 106, transmit and receive coefficient generators 108 and 110, and signal processor circuits 112 and 114. The circuit 100 can also be connected to further circuitry, such as a programmed computer (not shown) which can provide further sophisticated programming including, but not limited to, FFT or other frequency domain analysis.

The transmitters 104, comprising four transmit amplifiers $122_i$ (for $i=1, \ldots, 4$), respectively receive transmit level signals through lines $120_i$, which can be connected to an external controller, such as a computer. Each of the amplifiers $122_i$ also receives a phase signal $124_i$ from a transmit phase control latch 126. The transmit phase control latch 126 receives information from which it produces the phase signals through the data lines 128 at a time designated through the data load signal line 130. Data lines 128 and data load signal line 130 are also connected to an external controller. The audio select amplifier 132 is connected to an external conventional speaker (not shown) through a speaker line 136.

In response to a signal delivered from an external controller over the transmit clock line 138, each of the amplifiers $122_i$ produces a pulse having a predetermined amplitude and phase over a bidirectional transmit/-receive line $140_i$ which is connected to a separate one of the concentric annular elements $66_i$ through connector 102.

In response to the pulses transmitted toward a patient's ascending aorta through the suprasternal notch by the concentric annular elements $66_i$, the ultrasonic transducers 64 and the concentric annular elements $66_i$ receive pulses. The pulses received through the ultrasonic transducers 64 are respectively sent, via lines $142_i$, to the radio frequency (RF) amplifiers and demodulators $144_i$. The pulses received through the ultrasonic transducers 66$i$ are respectively sent, via bidirectional lines 142$_i$ to the RF amplifiers and demodulators 146$_i$. The RF amplifiers and demodulators 144$_i$ and 146$_i$ are included in the receiver circuitry 106.

The demodulator section of each of the RF amplifiers and demodulators 144$_i$ and 146$_i$ is connected to a double-output conventional phase-shifted source (not shown) of the transmitted ultrasonic frequency, for example, 2 MHz. One of the outputs is shifted by ninety degrees with respect to the other. The signals produced by the RF amplifiers and demodulators 144$_i$ and 146$_i$ are the direct and quadrature components of the Doppler modulated frequency signals corresponding to the velocity of blood measured by each of the elements in the device 60.

The direct and quadrature signals produced by the RF amplifiers and demodulators 146$_i$ are respectively sent over lines 148D$_i$ and 148Q$_i$ to attenuators in the coefficient generator 108. The signals sent over lines 148D$_1$ and 148Q$_1$ are both sent to attenuators 152W0 and 152N0. The signals sent over lines 148D$_2$ and 148Q$_2$ are both sent to attenuators 152W1 and 152N1. The signals sent over lines 148D$_3$ and 148Q$_3$ are both sent to attenuators 152W2 and 152N2. The signals sent over lines 148D$_4$ and 148Q$_4$ are both sent to attenuators 152W3 and 152N3.

Similarly, the direct and quadrature signals produced by the RF amplifiers and demodulators 144$_x$ are respectively sent over lines 150D$_x$ and 150Q$_x$ to attenuators in the coefficient generator 108, where x=N, S, E, or W. The signals sent over lines 150D$_x$ and 150Q$_x$ are respectively sent to attenuator 154X, which is comprised of attenuator sections 154×1 and 154×2. The attenuators 154×are contained in receive coefficient generator 110.

The attenuators 152 and 154 are each connected to the data bus 134 which transmits appropriate eight-bit weighting data to the attenuator which is selected through the 27-bit DATA LOAD signal on line 156. This signal is also received by the receive phase control latch 160 which receives therefrom the values of eight phases, P$_j$, for j=0, ..., 7, which are respectively used to adjust the phase of the signals produced by attenuators 152W0, 152N0, 152W1, 152N1, 152W2, 152N2, 152W3, and 152N3 through phase shifters 162$_j$. The phases P$_j$ may take only the values of 0 and 180 degrees. The phase-shifted signals produced by phase-shifting the direct signals 148D$_k$ through the phase shifters 160$_0$, 160$_2$, 160$_4$, and 160$_6$ are added in adder 164WD. Also, the phase-shifted signals produced by phase-shifting the quadrature signals 148Q$_k$ through the phase shifters 160$_0$, 160$_2$, 160$_4$, and 160$_6$ are added in adder 164WQ. Further, the phase-shifted signals produced by phase-shifting the direct signals 148D$_k$ through the phase shifters 160$_1$, 160$_3$, 160$_5$, and 160$_7$ are added in adder 164ND. Finally, the phase-shifted signals produced by phase-shifting the quadrature signals 148Q$_k$ through the phase shifters 160$_1$, 160$_3$, 160$_5$, and 160$_7$ are added in adder 164NQ. The adders 164 are located in the coefficient generator 108.

The signals produced by the coefficient generator 108 are processed by the signal processor 112, which includes sample-and-hold and band-pass filter units 166$_1$ and 166$_2$. The sample-and-hold and band-pass filter unit 166$_1$ operates on the direct and quadrature signals respectively produced by the adders 164WD and 164WQ. Similarly, the sample-and-hold and band-pass filter unit 166$_2$ operates on the direct and quadrature signals respectively produced by the adders 164ND and 164NQ.

The signals produced by the coefficient generator 110 are processed by the signal processor 114, which includes sample-and-hold and band-pass filter units 168$_1$, 168$_2$, 168$_3$, and 168$_4$. The sample-and-hold and band-pass filter unit 168$_1$ operates on the direct and quadrature signals respectively produced by the attenuators 154E1 and 154E2. Also, the sample-and-hold and band-pass filter unit 168$_2$ operates on the direct and quadrature signals respectively produced by the attenuators 154W1 and 154W2. Further, the sample-and-hold and band-pass filter unit 168$_3$ operates on the direct and quadrature signals respectively produced by the attenuators 154S1 and 154S2. Finally, the sample-and-hold and band-pass filter unit 168$_4$ operates on the direct and quadrature signals respectively produced by the attenuators 154N1 and 154N2.

The sample-and-hold and band-pass filter units 166$_1$, 166$_2$, 168$_1$, 168$_2$, 168$_3$, and 168$_4$ each receive sample-and-hold timing signals on the three-bit sample-and-hold line 170. These units 166 and 168 also each receive high-and low-pass clock signals respectively on lines 172 and 174.

The signals produced by the signal processors 112 and 114 are sent to further signal-processing circuitry, such as a programmed computer (not shown) which can perform such advanced signal-processing techniques as fast Fourier transform analyses, through lines 176. The signals produced by the signal processors 112 and 114 are also sent to audio select amplifier 132 which also receives data through the data bus 134 in response to the 27-bit DATA LOAD signal on line 156, and to the three-bit CHANNEL SELECT signal on line 180, which is connected to an external controller.

Alternative Embodiments

FIG. 14 is a plan view of a second embodiment of an ultrasonic device in accordance with the present invention. In this second embodiment, the first array 62 is comprised of three concentric annular elements 62$_i$, for i=1 to 3, and the aiming elements 64$_j$, j=1 to 4. The rationale is that the wider four-element annulus will allow a narrower narrow beam at the expense of diminished separation of the fields of the aiming beams. The aiming elements 64$_j$, which are also the second array 64, are each a ninety degree sector of the outermost annulus of the first array. These sectors will be used to receive the Doppler signals which emanate primarily from each quadrant of the wide sample volume. The innermost element 62$_1$ is circular, with an outer diameter of approximately 1.50 millimeters. The second element 62$_2$ is annular, with an outer diameter of approximately 3.20 millimeters. The third element 62$_3$ is also annular, with an outer diameter of approximately 7.00 millimeters. The outermost element 64, consisting of the elements 64$_j$, has an outer diameter of approximately 11.0 millimeters. When they form part of first array 62, the elements 64$_j$ are connected together electrically. When the elements 64$_j$ are part of the second array 64, the signals from the elements 64$_j$ be processed separately.

FIG. 15 is a elevation view of a third embodiment of the present invention. In this embodiment, the composite piezoelectric material comprising the device 60 is divided into arrays of ultrasonic elements as discussed in the foregoing, and each element is connected to an amplifier (not shown in FIG. 15) through "hot" leads 200$_i$. Also, the piezoelectric material is grounded through a ground lead 202. The leads 200$_i$ and 202 are connected to a printed circuit board (PCB) after passing through an air-like backing material which supports, and provides a proper ultrasonic impedance match to the nontransmitting side 204 of the device 60. The PCB is used as a place to make the electrical connections necessary to transmit signals to and from the composite piezoelectric material 60. The transmitting side 206 is faced with a quarter-wave matching layer 208 which is matched to the wavelength of the transmitted ultrasonic frequency to maximize the efficiency of the ultrasonic transducers that are included in the ultrasonic device. The lensing material (made from silicon rubber) serves to cant the received fields of the aiming transducers. A typical cant angle is 5 degrees.

The invention will also be useful for aligning simple Doppler velocimeters with various biological vessels. The ability to center Doppler sample volumes of defined shape within biological vessels will allow for more precise and stable blood velocity measurements, as is described in U.S. Pat. No. 4,796,634, issued to Huntsman et al.

For instance, it may prove that 2-D echo image estimates of aortic diameter will be more readily available as echo imagers become more ubiquitous in the critical care environment. If this is the case, a widebeam, pulsed Doppler velocimeter (as opposed to flowmeter) which is aimed at the aorta from the suprasternal notch could provide the estimate of the mean aortic velocity integral that is necessary to make accurate cardiac output calculations. The current invention would be very useful in such a device, since the uniform insonification of the aorta that is necessary to achieve an accurate mean velocity estimate would be hard to obtain unless an aiming mechanism can be provided. (Errors in cardiac output measurements could be expected to result from the velocity underestimations that occur due to the angle of incidence of the ultrasound beam. This error can be minimized if the technique described in this application is used to identify the sample depth at which the angle of incidence is lowest.)

While the detailed description above has been expressed in terms of a specific example, those skilled in the art will appreciate that many other circuits could be used to accomplish the purpose of the disclosed inventive apparatus. Accordingly, it can be appreciated that various modifications of the above-described embodiments may be made without departing from the spirit and the scope of the invention. Therefore, the spirit and the scope of the present invention are to be limited only by the following claims.

We claim:

1. A method for locating the flow of a fluid through a vessel in a body, comprising the steps of:
   (a) producing a first ultrasonic transducer having a first directivity pattern;
   (b) producing a second transducer, including an array of transducer elements, each transducer element having a distinct directivity pattern which is different from the directivity pattern of the first transducer;
   (c) generating a transmitting signal;
   (d) driving the first ultrasonic transducer by said transmitting signal to transmit ultrasonic energy into the body;
   (e) receiving the transmitted ultrasonic energy that is reflected within the body through each transducer element in the second ultrasonic transducer;
   (f) producing a received signal from the ultrasonic energy received by each transducer element in the second transducer; and
   (g) processing the received signals to produce a signal representative of a direction to move the first transducer to locate the flow of the fluid.

2. The method of claim 1, wherein step (g) includes the step of comparing the ultrasonic energy received by each of the transducer elements in the second array.

3. The method of claim 1, wherein step (b) includes producing at least three transducer elements in the second ultrasonic transducer and step (f) includes producing a received signal indicative of the amount of ultrasonic energy received by the corresponding transducer element.

4. The method of claim 3, wherein step (b) includes producing the transducer elements in the second ultrasonic array in opposing pairs of transducer elements whose directivity patterns are symmetric with respect to the first directivity pattern.

5. The method of claim 4, wherein step (g) includes comparing the ultrasonic energy received by the two transducer elements in each opposing pair of transducers and producing a signal representative of the direction to move the first transducer, moving the first array in said direction causing the ultrasonic energies received by the two transducer elements in each opposing pair of transducers to be more nearly equal.

6. The method of claim 4, further comprising the step of (h) producing an indication signal when the amount of ultrasonic energy received by both transducer elements in each pair of transducers in the second array cannot be made substantially equal.

7. The method of claim 3, wherein step (b) includes producing the transducer elements in the second transducer array so that their directivity patterns are symmetric with respect to the first directivity pattern.

8. The method of claim 7, wherein step (b) includes producing the transducer elements in the second transducer array so that their directivity patterns are directed outwardly from the first directivity pattern.

9. The method of claim 7, wherein step (b) further includes producing the transducer elements in the second transducer array in opposing pairs of transducer elements whose directivity patterns are symmetric with respect to the first directivity pattern.

10. The method of claim 9, wherein step (g) includes comparing the ultrasonic energy received by the two transducer elements in each opposing pair of transducers and producing a signal representative of the direction to move the first transducer, moving the first array in said direction causing the ultrasonic energies received by the two transducer elements in each opposing pair of transducers to be more nearly equal.

11. The method of claim 1, further comprising the step of placing the first transducer and second transducer array in fixed relationship to one another.

12. The method of claim 1, wherein the transmitting signal is a pulsed signal having predetermined times of occurrence.

13. The method of claim 12, wherein step (e) comprises receiving the reflected ultrasonic energy that returns after a predetermined delay time following the time of occurrence of the transmitting signal.

14. The method of claim 1, further comprising the step of:
   (h) measuring the flow of the fluid through the vessel.

15. The method of claim 1, further comprising the step of:
 (h) measuring a velocity of the fluid through the vessel.

16. The method of claim 1, wherein step (a) includes producing a first ultrasonic transducer comprising a plurality of first transducer elements and having a first directivity pattern.

17. A method for locating the flow of a fluid through a vessel in a body, comprising the steps of:
 (a) producing a first ultrasonic transducer having a first directivity pattern;
 (b) producing a second transducer, including an array of transducer elements in fixed relation relative to the first ultrasonic transducer, each transducer element having a distinct directivity pattern which is different from the directivity pattern of the first transducer, the transducer elements in the second transducer array being arranged so that their directivity patterns are symmetric with respect to the first directivity pattern;
 (c) generating a pulsed signal having predetermined times of occurrence;
 (d) driving the first ultrasonic transducer by said transmitting signal to transmit ultrasonic energy into the body;
 (e) receiving the transmitted ultrasonic energy that is reflected within the body through each transducer element in the second ultrasonic transducer after a predetermined delay time following the time of occurrence of the transmitting signal;
 (f) producing a received signal from the ultrasonic energy received by each transducer element in the second transducer; and
 (g) processing the received signals to produce a signal representative of a direction to move the first transducer to locate the flow of the fluid.

18. The method of claim 17, wherein step (b) includes the step of producing at least three transducer elements in the second ultrasonic transducer.

19. The method of claim 17, wherein step (b) includes producing the transducer elements in the second ultrasonic array in opposing pairs of transducer elements whose directivity patterns are symmetric with respect to the first directivity pattern.

20. The method of claim 17, wherein step (g) includes comparing the ultrasonic energy received by the two transducer elements in each opposing pair of transducers and producing a signal representative of the direction to move the first transducer, moving the first array in said direction causing the ultrasonic energies received by the two transducer elements in each opposing pair of transducers to be more nearly equal.

21. The method of claim 17, wherein step (b) includes producing the transducer elements in the second transducer array so that their directivity patterns are symmetric with respect to the first directivity pattern.

22. The method of claim 17, wherein step (b) includes producing the transducer elements in the second transducer array so that their directivity patterns are directed outwardly from the first directivity pattern.

23. The method of claim 17, wherein step (a) includes producing a first ultrasonic transducer comprising a plurality of first transducer elements and having a first directivity pattern.

24. The method of claim 17, further comprising the step of:
 (h) measuring the flow of the fluid through the vessel.

25. The method of claim 17, further comprising the step of:
 (h) measuring a velocity of the fluid through the vessel.

26. A method for locating the flow of a fluid through a vessel in a body, comprising the steps of:
 (a) producing a first ultrasonic transducer comprising a plurality of first transducer elements and having a first directivity pattern;
 (b) producing a second transducer, including an array of at least four transducer elements in opposing pairs of transducer elements in fixed relation relative to the first ultrasonic transducer, each transducer element in the second transducer having a distinct directivity pattern which is different from the directivity pattern of the first transducer, the transducer elements in the second transducer array being arranged so that their directivity patterns are directed outwardly from the first directivity pattern;
 (c) generating a pulsed signal having predetermined times of occurrence;
 (d) driving the first ultrasonic transducer by said transmitting signal to transmit ultrasonic energy into the body;
 (e) receiving the transmitted ultrasonic energy that is reflected within the body through each transducer element in the second ultrasonic transducer after a predetermined delay time following the time of occurrence of the transmitting signal;
 (f) producing a received signal from the ultrasonic energy received by each transducer element in the second transducer; and
 (g) processing the received signals to produce a signal representative of a direction to move the first transducer to locate the flow of the fluid.

27. The method of claim 26, wherein step (g) includes comparing the ultrasonic energy received by the two transducer elements in each opposing pair of transducers and producing a signal representative of the direction to move the first transducer, moving the first array in said direction causing the ultrasonic energies received by the two transducer elements in each opposing pair of transducers to be more nearly equal.

28. The method of claim 26, further comprising the step of:
 (h) measuring the flow of the fluid through the vessel.

29. The method of claim 26, further comprising the step of:
 (h) measuring a velocity of the fluid through the vessel.

30. A method for locating the flow of a fluid through a vessel in a body, comprising the steps of:
 (a) producing a first ultrasonic transducer comprising a plurality of first transducer elements and having a first directivity pattern;
 (b) producing a second transducer, including an array of at least four transducer elements in opposing pairs of transducer elements in fixed relation relative to the first ultrasonic transducer, each transducer element having a distinct directivity pattern which is different from the directivity pattern of the first transducer, the transducer elements in the second transducer array being arranged so that their directivity patterns are directed outwardly from and symmetric with respect to the first directivity pattern;

(c) generating a pulsed signal having predetermined times of occurrence;
(d) driving the first ultrasonic transducer by said transmitting signal to transmit ultrasonic energy into the body;
(e) receiving the transmitted ultrasonic energy that is reflected within the body through each transducer element in the second ultrasonic transducer after a predetermined delay time following the time of occurrence of the transmitting signal;
(f) producing a received signal from the ultrasonic energy received by each transducer element in the second transducer; and
(g) processing the received signals to produce a signal representative of a direction to move the first transducer to locate the flow of the fluid.

31. The method of claim 30, wherein step (g) includes comparing the ultrasonic energy received by the two transducer elements in each opposing pair of transducers and producing a signal representative of the direction to move the first transducer, moving the first array in said direction causing the ultrasonic energies received by the two transducer elements in each opposing pair of transducers to be more nearly equal.

32. The method of claim 30, further comprising the step of (h) producing an indication signal when the amount of ultrasonic energy received by both transducer elements in each pair of transducers in the second array cannot be made substantially equal.

33. The method of claim 30, further comprising the step of:
(h) measuring the flow of the fluid through the vessel.

34. The method of claim 30, further comprising the step of:
(h) measuring a velocity of the fluid through the vessel.

* * * * *